(12) United States Patent
Lindemann et al.

(10) Patent No.: US 11,918,672 B2
(45) Date of Patent: Mar. 5, 2024

(54) WATER BASED CONCENTRATED PRODUCT FORMS OF OIL-SOLUBLE ORGANIC UV ABSORBERS

(71) Applicant: BASF SE, Ludwigshafen am Rhein (DE)

(72) Inventors: Brigitte Lindemann, Grenzach-Wyhlen (DE); Stefan Busch, Düsseldorf-Holthausen (DE); Frank Pirrung, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 195 days.

(21) Appl. No.: 16/642,999

(22) PCT Filed: Aug. 28, 2018

(86) PCT No.: PCT/EP2018/073127
§ 371 (c)(1),
(2) Date: Feb. 28, 2020

(87) PCT Pub. No.: WO2019/042999
PCT Pub. Date: Mar. 7, 2019

(65) Prior Publication Data
US 2020/0337974 A1    Oct. 29, 2020

(30) Foreign Application Priority Data
Sep. 1, 2017   (EP) ..................................... 17189009

(51) Int. Cl.
| A61K 8/49 | (2006.01) |
| A61K 8/362 | (2006.01) |
| A61K 8/37 | (2006.01) |
| A61K 8/46 | (2006.01) |
| A61K 8/60 | (2006.01) |
| A61K 8/81 | (2006.01) |
| A61Q 17/04 | (2006.01) |

(52) U.S. Cl.
CPC ............ *A61K 8/4966* (2013.01); *A61K 8/362* (2013.01); *A61K 8/37* (2013.01); *A61K 8/463* (2013.01); *A61K 8/602* (2013.01); *A61K 8/8147* (2013.01); *A61Q 17/04* (2013.01)

(58) Field of Classification Search
CPC ............................. A61Q 17/04; A61K 8/4966
See application file for complete search history.

(56) References Cited

U.S. PATENT DOCUMENTS

| 5,108,654 A | 4/1992 | Ragaini |
| 5,252,323 A | 10/1993 | Richard et al. |
| 5,332,568 A | 7/1994 | Raspanti |
| 5,520,906 A | 5/1996 | Stein et al. |
| 8,580,876 B2 * | 11/2013 | Pirrung ................ C08K 5/005 524/270 |
| 9,044,623 B2 * | 6/2015 | Musa ...................... A61K 8/30 |
| 2003/0059383 A1 | 3/2003 | Sanogueira et al. |
| 2010/0129303 A1 * | 5/2010 | Dueva-Koganov ...... A61K 8/72 424/60 |
| 2010/0284950 A1 * | 11/2010 | Muller ..................... A61K 8/37 424/59 |
| 2011/0064681 A1 * | 3/2011 | Wendel ................ C08G 18/10 424/59 |
| 2014/0227205 A1 | 8/2014 | Mendrok-Edinger |
| 2016/0067158 A1 * | 3/2016 | Hloucha ................. A61K 8/33 |
| 2017/0027835 A1 | 2/2017 | Ehlis et al. |

FOREIGN PATENT DOCUMENTS

| CN | 101686909 A | 3/2010 |
| CN | 106163492 A | 11/2016 |
| EP | 0517104 A1 | 12/1992 |
| GB | 2286774 A | 8/1995 |
| JP | 2007247089 A | 9/2007 |
| JP | 2007247089 A | 9/2007 |
| WO | WO-9317002 A1 | 9/1993 |
| WO | 97/03642 A1 | 2/1997 |
| WO | WO-200523878 A1 | 3/2005 |
| WO | 2009007264 A2 | 1/2009 |
| WO | WO-2009007264 A2 | 1/2009 |
| WO | 2011/042087 A2 | 4/2011 |
| WO | 2011/042089 A2 | 4/2011 |
| WO | 2016/206963 A1 | 12/2016 |

OTHER PUBLICATIONS

Canselier, et al., "Ultrasound Emulsification—An Overview", Journal of Dispersion Science and Technology, vol. 23, Issue 1-3, 2002, pp. 333-349.

(Continued)

*Primary Examiner* — Mark V Stevens
*Assistant Examiner* — Alparslan Asan
(74) *Attorney, Agent, or Firm* — Faegre Drinker Biddle & Reath LLP

(57) ABSTRACT

An aqueous polymer dispersion with an average particle size of less than 1000 nm comprising a) a polymer carrier prepared by heterophase radical polymerization of at least one ethylenically unsaturated monomer in the presence of b) an oil-soluble organic UV absorber selected from the class of p-aminobenzoic acid derivatives; salicylic acid derivatives; benzophenone derivatives; diphenyl acrylate derivatives; benzofuran derivatives; polymeric UV absorbers, comprising one or more organosilicon radicals; cinnamic acid derivatives; camphor derivatives; s-triazine derivatives; trianilino-striazine derivatives; menthyl anthranilates; and benzotriazole derivatives; wherein the weight ratio of the oil-soluble organic UV absorber (b) to polymer carrier (a) is greater than 50 parts UV absorber per 100 parts of carrier; and c) a surfactant selected from $c_1$) a nonionic surfactant selected from $c_{11}$) the condensation product of a $C_6$ to $C_{18}$ fatty alcohol or $C_6$ to $C_{18}$ fatty acid and a mono- or disaccharide; and $c_2$) an anionic surfactant selected from $c_{21}$) sulfosuccinates and sulfosuccinamates; $c_{22}$) fatty alcoholates; and $c_{23}$) mixtures of phosphoric acid esters and fatty alcohols having from 6 to 18, preferably from 8 to 10, carbon atoms. The aqueous polymer dispersions show unexpectedly high sunscreen effects and a positive skin feeling. They have excellent anti-pollen, anti-dust and anti-oxidant performances in sun screen compositions.

5 Claims, 2 Drawing Sheets

(56) References Cited

OTHER PUBLICATIONS

Figure 1:
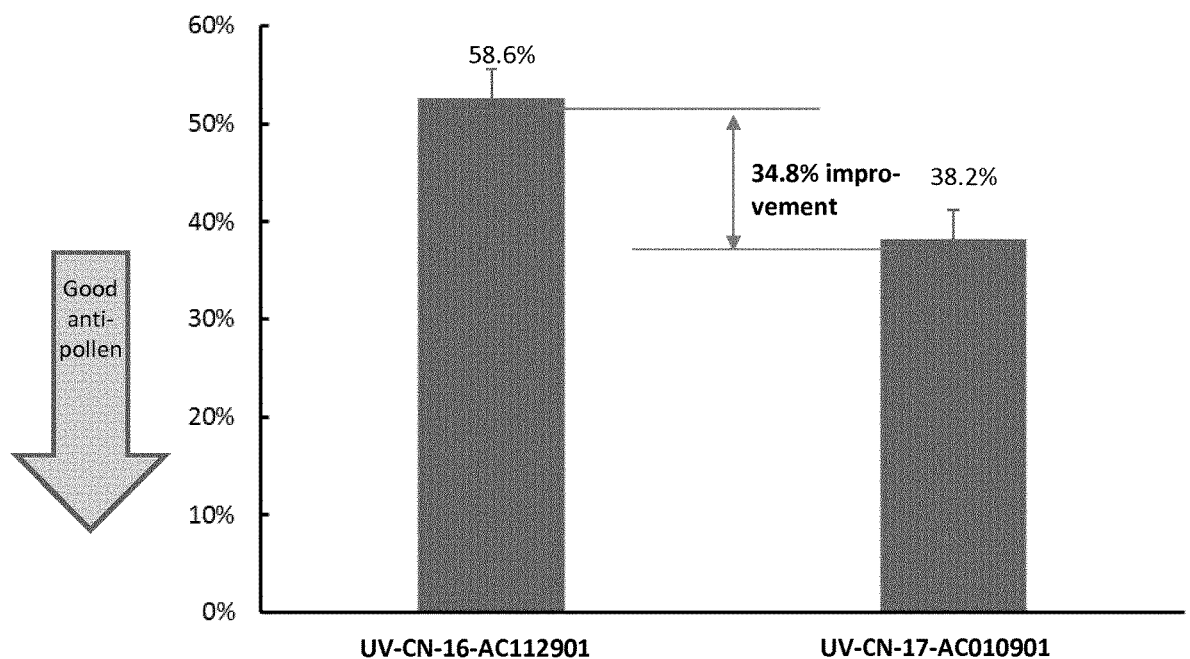

Dr. Martin Wloka, "Paper 12—An in-Vitro SPF Screening approach considering the photostability of the UV Filters", 2010—A Sun Odyssey, International Conference, Jun. 8-9, 2005, 18 pages.
European Search Report for EP Patent Application No. 17189009.8, dated Jan. 23, 2018, 3 pages.
International Preliminary Report on Patentability received for PCT Patent Application No. PCT/EP2018/073127, dated Mar. 12, 2020, 11 pages.
Meylan, et al., "Atom/fragment contribution method for estimating octanol-water partition coefficients", Journal of Pharmaceutical Sciences, vol. 84, Issue 1, Jan. 1995, pp. 83-92.
International Search Report for PCT/EP2018/073127 dated Nov. 28, 2018.
Written Opinion of the International Searching Authority for PCT/EP2018/073127 dated Nov. 28, 2018.
Kuhn, Darl, Compositions with Beneficial Properties for Customers ed-ip.com, ip.com Inc. Jul. 17, 2017, XP013175395 ISSN: 1533-0001, 29 pages.
Kuhn, Darl, "Sun Care with Reduced Fabric Staining", op. com, ip.com Inc. May 30, 2017, XP01317508, ISSN: 1533-0001, 90 pages.
Article 94(3) EPC received for EP applciaton No. 18756470.3 mailed on May 11, 2022, 10 pages.

\* cited by examiner

WATER BASED CONCENTRATED PRODUCT FORMS OF OIL-SOLUBLE ORGANIC UV ABSORBERS

CROSS-REFERENCE TO RELATED APPLICATIONS

This application is a national stage application (under 35 U.S.C. § 371) of PCT/EP2018/073127, filed Aug. 28, 2018, which claims benefit of European Application No. 171.89009.8, filed Sep. 1, 2017, both of which are incorporated herein by reference in their entirety.

The instant invention pertains to an aqueous polymer dispersion with a particle size of less than 1000 nm containing specific oil-soluble organic UV absorbers, prepared by hetero phase radical polymerization of ethylenically unsaturated monomers in the presence of said UV absorbers, wherein the weight ratio of UV absorbers to polymeric carrier is greater than 50 parts UV absorbers per 100 parts polymer carrier.

Another aspect of the invention is a process for the preparation of such aqueous polymer dispersions with UV absorber content. Aqueous dispersions prepared according to this process are useful ingredients for cosmetic applications, preferably sunscreens.

A further aspect of the invention is the use of the aqueous polymer dispersion in cosmetic compositions to produce an anti-pollen effect.

Another aspect of the invention is the use of the aqueous polymer dispersion in cosmetic compositions to provide an anti-oxidant effect on the skin.

An additional aspect of the invention is the use of the aqueous polymer dispersion in cosmetic compositions to reduce particle adhesiveness on the skin.

Only a small number of registered UV filters exist for cosmetic UV protection in the aqueous phase. Unfortunately, the use of these UV absorbers is highly limited. For example, the well-known UV absorber Phenylbenzimidazole Sulfonic Acid (PBSA) can only be used in a very small pH range >7.2. Formulations featuring a skin neutral pH are therefore not accessible with these UV filters.

Simultaneously it is well known that the balanced combination of UV filters in the oil- and water phase shows a particular high protection effect compared to formulations which comprise only UV filters in the oil- or water phase. Such formulations, however, show only little water resistance.

It has now been found that concentrated aqueous polymer dispersions with a particle size of less than 1000 nm, which are prepared by heterophase radical polymerization of ethylenically unsaturated monomers in the presence of UV absorbers, wherein the weight ratio between UV absorber and polymer carrier is greater than 50 parts of UV absorber to 100 parts of the polymer carrier, show unexpectedly high sunscreen effects and a positive skin feeling.

The figures show in

Figure 2:
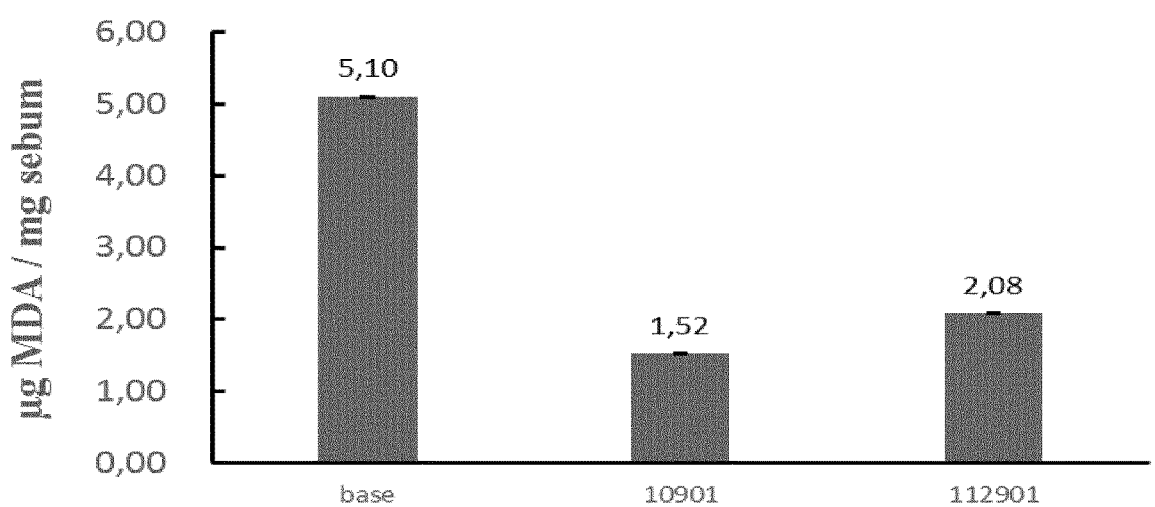
Figure 3:
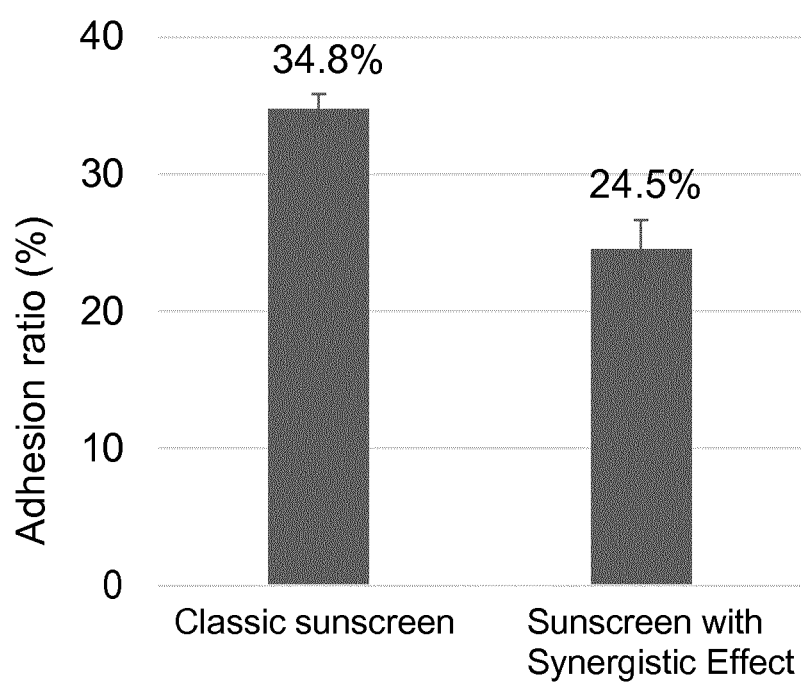

FIG. 1 a graph on the comparison of pollen adhesion ratio of sunscreen formulations FIG. 2 a graph on the comparison of anti-oxidation efficacy of sunscreen formulations FIG. 3 a graph on the comparison of sand adhesion ratio of sunscreen formulations One aspect of the invention is therefore an aqueous polymer dispersion with an average particle size of less than 1000 nm comprising (a) a polymer carrier prepared by heterophase radical polymerization of at least one ethylenically unsaturated monomer in the presence of (b) an oil-soluble organic UV absorber selected from the class of p-aminobenzoic acid derivatives; salicylic acid derivatives; benzophenone derivatives; diphenyl acrylate derivatives; benzofuran derivatives; polymeric UV absorbers, comprising one or more organosilicon radicals; cinnamic acid derivatives; camphor derivatives; s-triazine derivatives; trianilino-s-triazine derivatives; menthyl anthranilates; and benzotriazole derivatives; wherein the weight ratio of the oil-soluble organic UV absorber (b) to polymer carrier (a) is greater than 50 parts UV absorber per 100 parts of carrier; and (c) a surfactant selected from
$c_1$) a nonionic surfactant selected from
($c_{11}$) the condensation product of a $C_6$ to $C_{18}$ fatty alcohol or $C_6$ to $C_{18}$ fatty acid and a mono- or disaccharide; and
($c_2$) an anionic surfactant selected from
($c_{21}$) sulfosuccinates and sulfosuccinamates;
($c_{22}$) fatty alcoholates; and
($c_{23}$) mixtures of phosphoric acid esters and fatty alcohols having from 6 to 18, preferably from 8 to 10, carbon atoms.

Oil-soluble UV absorbers used as component (b) in the present invention are selected from different classes of well-known organic UV filters. Such protective substances are described, for example, in GB-A-2,286,774 or alternatively are known from Cosmetics & Toiletries (107), 50 et seq. (1992).

The following compounds are examples of p-aminobenzoic acid derivatives:

4-aminobenzoic acid (PABA); ethyldihydroxypropyl-PABA of formula

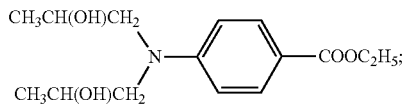

PEG-25-PABA of formula

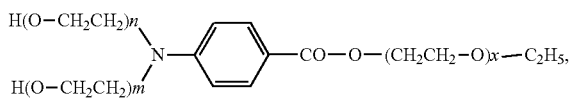

wherein m, n and x have the same meaning and are each a maximum of 25; octyldimethyl PABA of formula

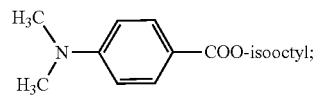

and glycyl aminobenzoate of formula

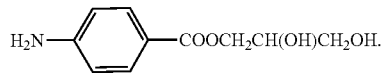

The following compounds are examples of salicylic acid derivatives:
homomenthyl salicylate of formula

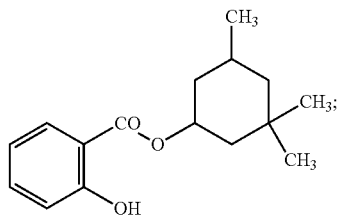 [SMILES: CC1CC(OC(=O)c2ccccc2O)CC(C)(C)C1]

triethanolamine salicylate of formula

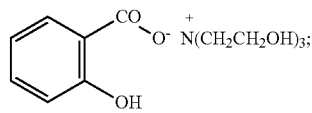

amyl p-dimethylaminobenzoate of formula

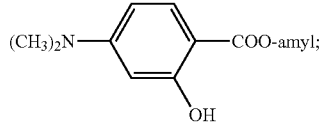

octyl salicylate of formula

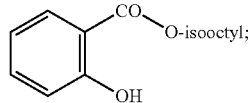

and
4-isopropylbenzyl salicylate of formula

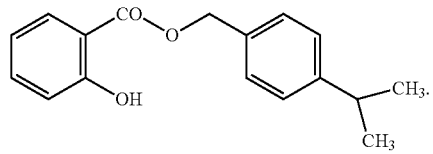

The following compounds are examples of benzophenone derivatives:
benzophenone-3-(2-hydroxy-4-methoxybenzophenone), benzophenone-4-(2-hydroxy-4-methoxybenzophenone-5-sulfonic acid) and benzophenone-8-(2,2'-dihydroxy-4-methoxybenzophenone).

The following compounds are examples of diphenyl acrylate derivatives:
octocyrlene (2-ethylhexyl-2-cyano-3,3'-diphenyl acrylate) and octocrylene (ethyl-2-cyano-3,3'-diphenyl acrylate).

The following compounds are examples of benzofuran derivatives:
3-(benzofuranyl)-(2-cyanoacrylate, 2-(2-benzofuranyl)-5-tert-butylbenzoxazole and 2-(p-aminophenyl)benzofuran and especially the compound of formula

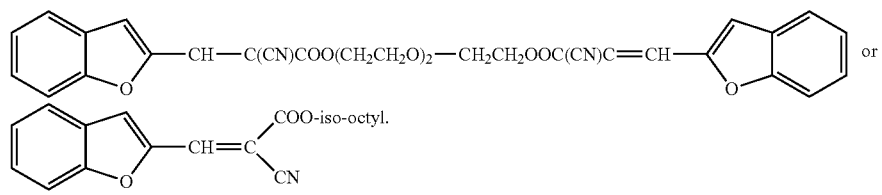

The following compounds are examples of polymeric UV absorbers that contain one or more organosilicon radicals:
a benzylidene malonate derivative, especially the compound of formula

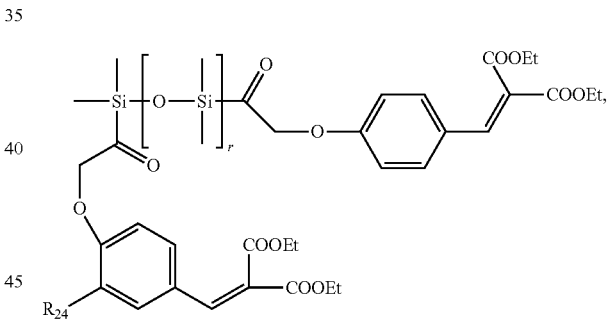

wherein $R_{24}$ is hydrogen or methoxy and r is approximately 7; the compound of formula

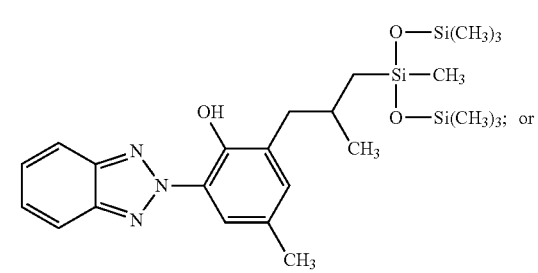

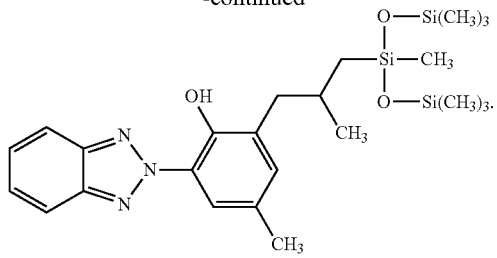

The following compounds are examples of cinnamic acid esters:

Octyl methoxycinnamate (4-methoxycinnamic acid 2-ethylhexyl ester), diethanolamine methoxycinnamate (diethanolamine salt of 4-methoxycinnamic acid), isoamyl p-methoxycinnamate (4-ethoxycinnamic acid 2-isoamyl ester), 2,5-diisopropylmethyl cinnamate and a cinnamic acid amido derivative.

The following compounds are examples of camphor derivatives:

4-methyl-benzylidene camphor [3-(4'-methyl)benzylidene-bornan-2-one], 3-benzylidene camphor (3-benzylidene-bornan-2-one), polyacrylamidomethyl-benzylidene camphor {N-[2(and 4)-2-oxyborn-3-ylidene-methyl)benzyl]acrylamide polymer}, trimonium-benzylidene camphor sulfate [3-(4'-trimethylammonium)-benzylidene-bornan-2-one methyl sulfate], terephthalydene dicamphorsulfonic acid {3,3'-(1,4-phenylenedimethine)-bis(7,7-dimethyl-2-oxo-bicyclo[2.2.1]heptane-1-methanesulfonic acid} or salts thereof, and benzylidene camphorsulfonic acid [3-(4'-sulfo)benzylidenebornan-2-one] or salts thereof.

The following compounds are examples of trianilino-s-triazine derivatives:

octyl triazine-[2,4,6-trianilino-(p-carbo-2'-ethyl-1'-oxy)-1,3,5-triazine, and the trianilino-s-triazine derivatives described in U.S. Pat. Nos. 5,332,568, 5,252,323, WO 93/17002 and WO 97/03642 and EP-A-0 517 104.

The following compound is an example of s-triazine compounds:

2-(4'-methoxyphenyl)-4,6-bis(2'-hydroxy-4'-n-octyloxyphenyl)-1,3,5-triazine; 2,4-bis{[4-(3-(2-propyloxy)-2-hydroxypropyloxy)-2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethylcarboxyl)phenylamino]-1,3,5-triazine; 2,4-bis{[4-(tris(trimethylsiloxysilylpropyloxy)-2-hydroxy]phenyl}-6-(4-methoxyphenyl)-1,3,5-triazine; 2,4-bis{[4-(2"methylpropenyloxy)-2-hydroxy]phenyl}-6-(4-methoxyphenyl)-1,3,5-triazine; 2,4-bis{[4-(1',1',1',3',5',5',5'-heptamethyltrisilyl-2"-methylpropyloxy)-2-hydroxy]phenyl}-6-(4-methoxyphenyl)-1,3,5-triazine; 2,4-bis{[4-(3-(2-propyloxy)-2-hydroxypropyloxy)-2-hydroxy]phenyl}-6-[4-ethylcarboxyl)-phenylamino]-1,3,5-triazine; or 2,4-bis{[4-(2-ethylhexyloxy)-2-hydroxy]phenyl}-6-(1-methylpyrrol-2-yl)-1,3,5-triazine.

The following compound is an example of a benzotriazole:

2-(2-hydroxy-5-methyl-phenyl)benzotriazole and Benzotriazolyl Dodecyl p-Cresol.

In a preferred embodiment of the present invention the following UV absorbers are used:

($b_1$) Ethylhexyl Methoxycinnnamate of formula (1)

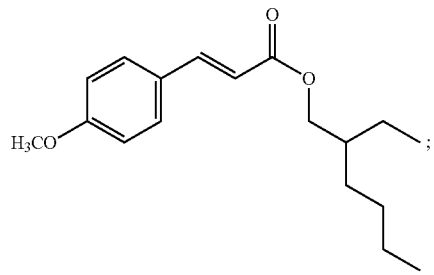 [SMILES: CCCCC(CC)COC(=O)/C=C/c1ccc(OC)cc1]

($b_2$) Bis-Ethylhexyloxyphenol Methoxyphenyl Triazine of formula (2)

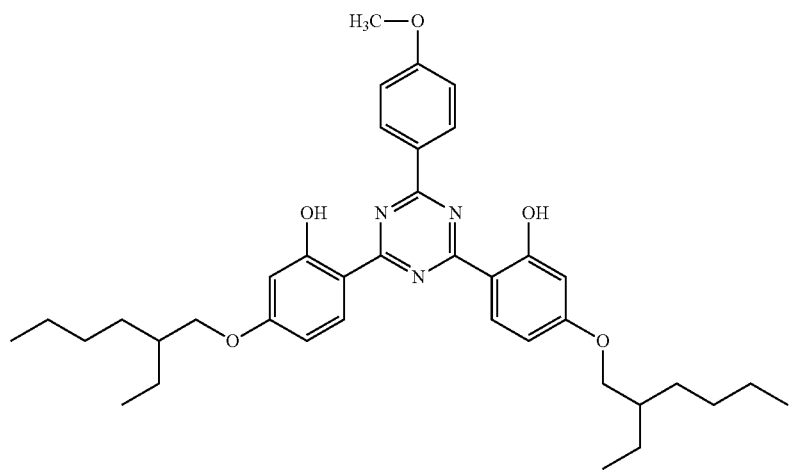 [SMILES: CCCCC(CC)COc1ccc(-c2nc(-c3ccc(OC)cc3)nc(-c3ccc(OCC(CC)CCCC)cc3O)n2)c(O)c1]

(b₃) Benzotriazolyl Dodecyl p-Cresol of formula (3)
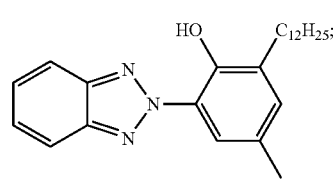
(b₄) Butyl Methoxydibenzoyl Methane of formula (4)
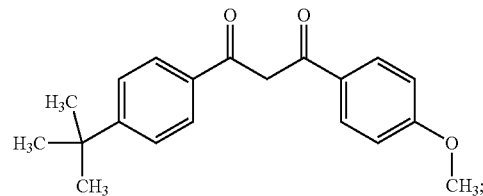 [SMILES: COc1ccc(C(=O)CC(=O)c2ccc(C(C)(C)C)cc2)cc1]
(b₅) 2-Cyan-3,3-diphenylacrylic acid (2-ethylhexylester) of formula (5)
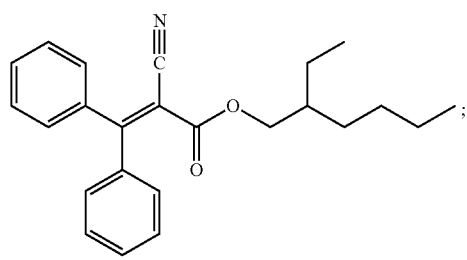 [SMILES: CCCCC(CC)COC(=O)C(C#N)=C(c1ccccc1)c1ccccc1]
(b₆) Tris-Ethylhexyloxyphenol Methoxyphenyl Triazine of formula (6)
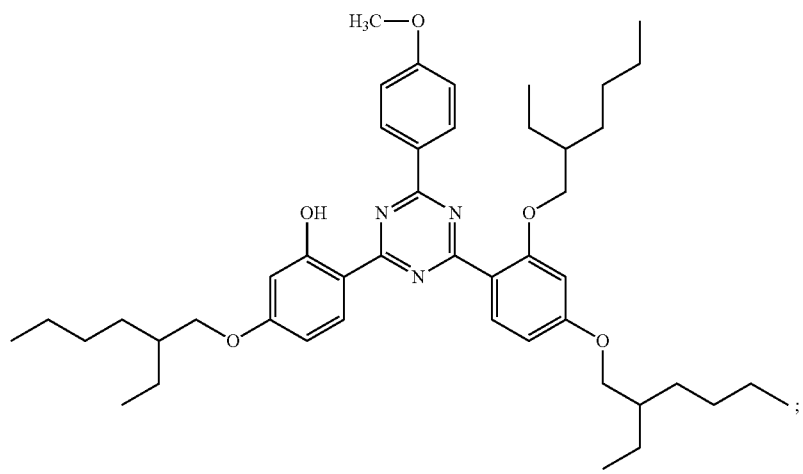 [SMILES: CCCCC(CC)COc1ccc(-c2nc(-c3ccc(OC)cc3)nc(-c3ccc(OCC(CC)CCCC)cc3OCC(CC)CCCC)n2)c(O)c1]
(b₇) Benzophenone-3 of formula (7)
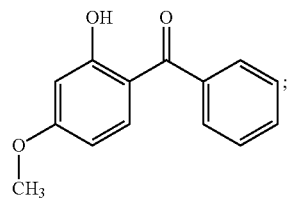 [SMILES: COc1ccc(C(=O)c2ccccc2)c(O)c1]
(b₈) Benzophenone-4 of formula (8)
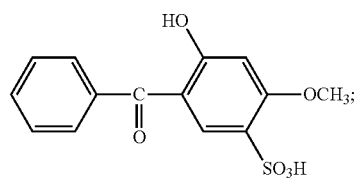 [SMILES: COc1cc(O)c(C(=O)c2ccccc2)cc1S(=O)(=O)O]

($b_9$) polysilicone-15 of formula (9)
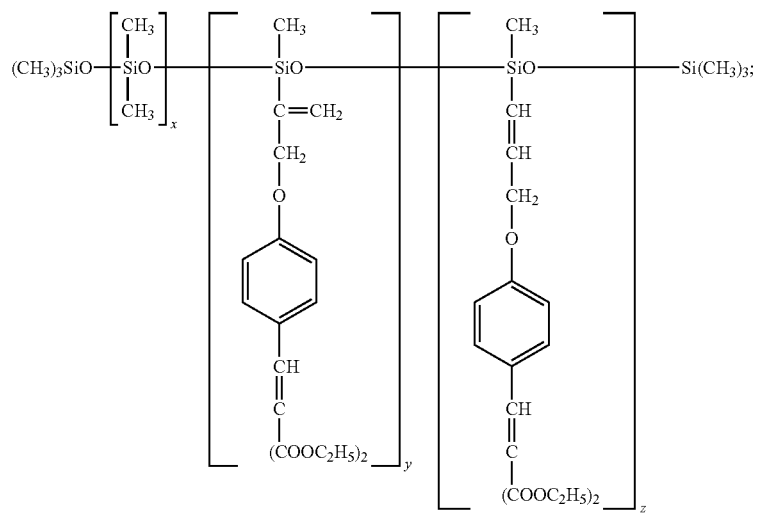
($b_{10}$) Diethylamino Hydroxy Benzoyl Hexyl Benzoate of formula (10)
($b_{12}$) Drometrizole Trisiloxane of formula (12)
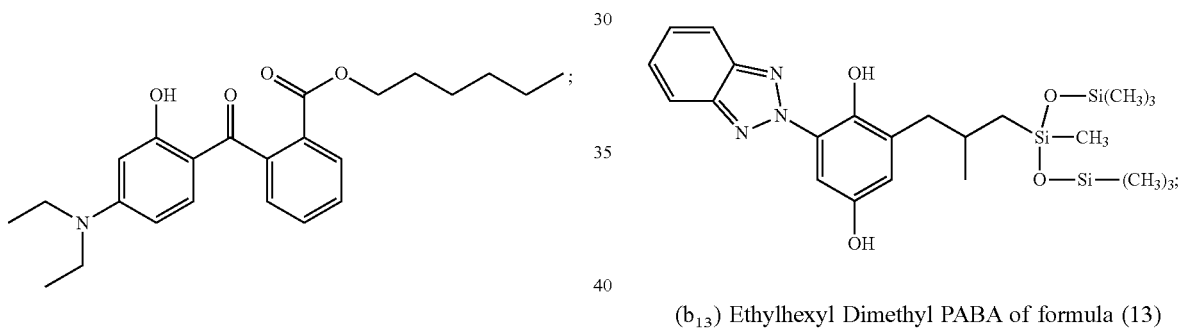
($b_{13}$) Ethylhexyl Dimethyl PABA of formula (13)
($b_{11}$) Diethylhexyl Butamido Triazone of formula (11)
($b_{14}$) Ethylhexyl Salicylate of formula (14)
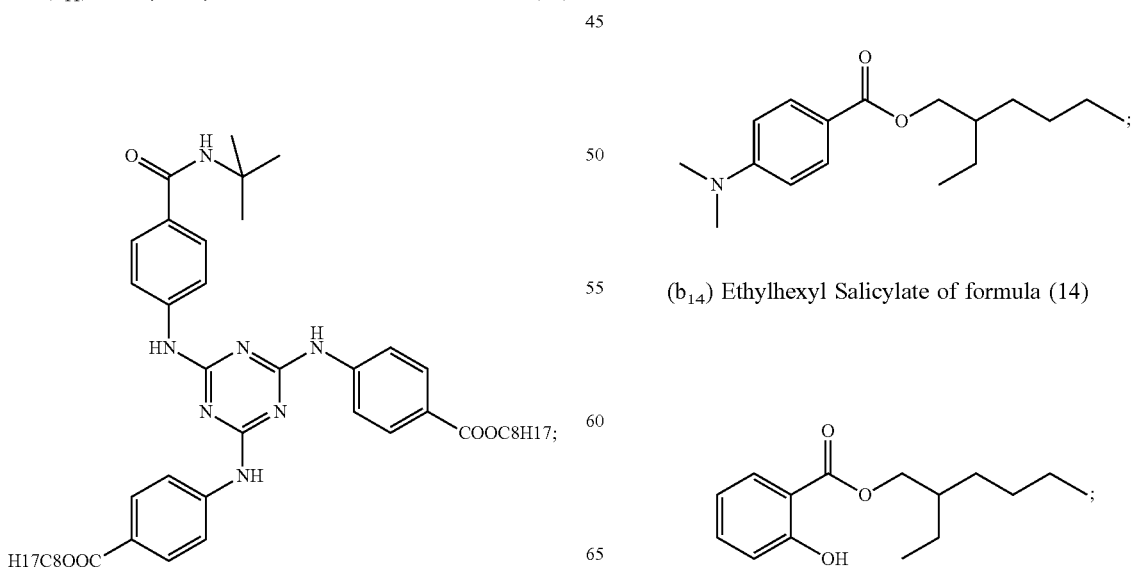

($b_{15}$) Ethylhexyl Triazone of formula

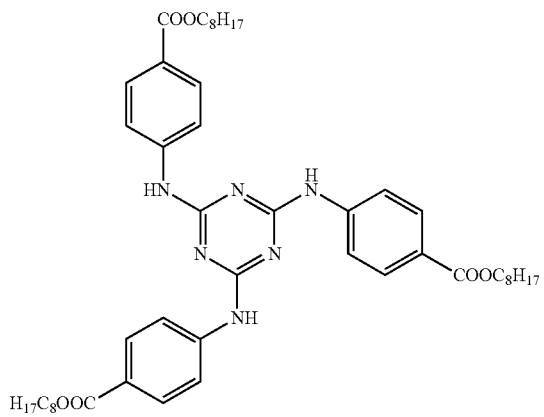

(15) ($b_{16}$) Homosalate of formula (16)

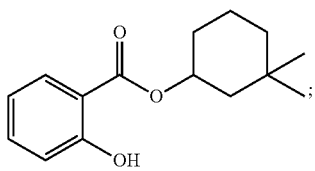 [SMILES: CC1(C)CCCC(OC(=O)c2ccccc2O)C1]

($b_{17}$) Isoamyl p-Methoxycinnamate of formula (17)

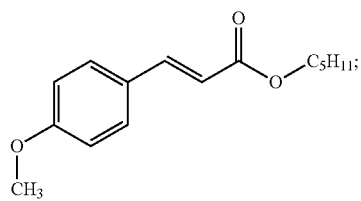

($b_{18}$) 4-Methylbenzylidene Camphor of formula (18)

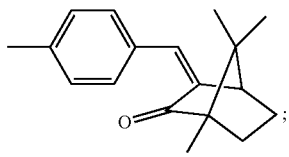 [SMILES: Cc1ccc(/C=C2\C(=O)C3(C)CCC2C3(C)C)cc1]

or mixtures of ($b_1$) to ($b_{18}$).

Preferably the UV absorber ($b_2$) of formula (2) is used in the present aqueous polymer dispersion.

Preferably the concentration of the polymer carrier comprising the oil-soluble organic UV absorber (b) in the dispersion is from 20% to 60% by weight.

Preferably more than one ethylenically unsaturated monomer is used for the heterophase radical polymerization. When the polymerization is carried out with two or more monomers, at least one may carry two unsaturated functionalities in order to provide a certain degree of crosslinking. For example, the amount of the resistance bifunctional monomer may vary from 0.1 to 20% by weight based on the total weight of the monomer mixture.

Preferred is the use of a concentrated aqueous polymer dispersion wherein the weight ratio of oil-soluble organic UV absorber to polymer carrier is equal or greater than 80 parts per 100 parts, more preferred greater 100 parts per 100 parts and most preferred greater 120 parts per 100 parts.

In a specific embodiment of the invention, the weight ratio of the oil-soluble UV absorber to polymer carrier is from 500 parts of the UV absorber per 100 parts of polymer carrier to 100 parts of the UV absorber to 100 parts of polymer carrier.

Preferably the average particle size is less than 500 nm, more preferably less than 250 nm.

Droplet (oil/water emulsion) as well as particle (polymer dispersion) size can be measured by using dynamic light scattering (DLS) technique (also known as photon correlation spectroscopy (PSC) or quasi-elastic light scattering (QELS). For this kind of measurement a particle sizer (NANO-flex® 180° DLS System, Particle Metrix GmbH, Meerbusch, Germany) with a fixed scattering angle of 90° or 180° can be used. The measurement leads to the mean diameter $D_{INT}$ (intensity weighted).

The total solids content of the concentrated aqueous polymer dispersion is for example 20%, for instance more than 30% and preferably more than 40% by weight based on the total weight of the aqueous dispersion. In a particularly preferred embodiment the total solids content is more than 45% by weight based on the total weight of the aqueous dispersion.

The organic UV absorber (b) has a water solubility of less than 1% preferably less than 0.1% and most preferably of less than 0.01% by weight at room temperature and atmospheric pressure.

The right balance between solubility in water and solubility in the monomer droplets influences strongly the polymerization result. Therefore, the polarity of the oil-soluble organic UV absorber can also be expressed in terms of log p.

The partition coefficient log p (octanol/water) is a widely used parameter for example in rating the environmental impact of chemical compounds. Its calculation is described by W. M. Meylan, P. H. Howard in J. Pharmaceutical Sciences 84, (1995), 83-92.

In the context of the present invention the oil-soluble organic UV absorber has a log p value of more than log p=2.

For example, the ethylenically unsaturated monomer is selected from the group consisting of styrene, substituted styrene, conjugated dienes, acrolein, vinyl acetate, vinyl pyrrolidone, vinylimidazole, maleic anhydride, (alkyl) acrylic acid anhydrides, (alkyl)acrylic acid salts, (alkyl) acrylic esters, (alkyl)acrylonitriles, (alkyl)acrylamides, vinyl halides or vinylidene halides.

For instance the ethylenically unsaturated monomer is a compound of formula $CH_2=C(R_a)-(C=Z)-R_b$, wherein Z is O or S; $R_a$ is hydrogen or $C_1$-$C_4$alkyl, $R_b$ is $NH_2$, O-($Me^+$), glycidyl, unsubstituted $C_1$-$C_{18}$alkoxy, $C_2$-$C_{10}$alkoxy interrupted by at least one N and/or O atom, or hydroxy-substituted $C_1$-$C_{18}$alkoxy, unsubstituted $C_1$-$C_{100}$alkylamino, di($C_1$-$C_{18}$alkyl)amino, hydroxy-substituted $C_1$-$C_{18}$alkylamino or hydroxy-substituted di($C_1$-$C_{18}$alkyl)amino, $-O-CH_2-CH_2-N(CH_3)_2$ or $-O-CH_2-CH_2-N^+H(CH_3)_2An^-$;

$An^-$ is an anion of a monovalent organic or inorganic acid;

Me is a monovalent metal atom or the ammonium ion.

Examples for specific ethylenically unsaturated monomers are styrene, iso-butylmethacrylate, cyclohexylmethacrylate, hydroxyethylmethacrylate, methylmethacrylate, benzyl methacrylate, vinyl toluene, n-butylacrylate, tert-butylacrylate, methylacrylate, ethylacrylate, propylacrylate, hexylacrylate or hydroxyethylacrylate.

Mixtures of ethylenically unsaturated monomers can also be used, for example mixtures of hydroxyethylmethacrylate, methylmethacrylate, cyclohexylmethacrylate, vinyl toluene, methylmethacrylate, iso-buylmethacrylate or mixtures of methylmethacrylate, stearylmethacrylate and methacrylic acid.

Examples of acids from which the anion $An^-$ is derived are $C_1$-$C_{12}$carboxylic acids, organic sulfonic acids such as $CF_3SO_3H$ or $CH_3SO_3H$, mineralic acids such as HCl, HBr or HI, oxo acids such as $HClO_4$ or complex acids such as $HPF_6$ or $HBF_4$.

Examples for $R_a$ as $C_2$-$C_{100}$alkoxy interrupted by at least one O atom are of formula

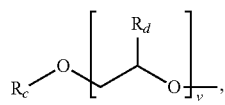

wherein $R_c$ is $C_1$-$C_{25}$alkyl, phenyl or phenyl substituted by $C_1$-$C_{18}$alkyl, and $R_d$ is hydrogen or methyl and v is a number from 1 to 50.

These monomers are for example derived from non-ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

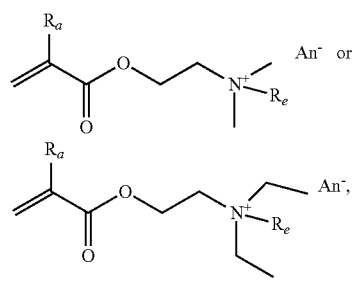

wherein $An^-$ and $R_a$ have the meaning as defined above and $R_e$ is methyl or benzyl. $An^-$ is preferably $Cl^-$, $Br^-$ or $-O_3S-CH_3$.

Further acrylate monomers are

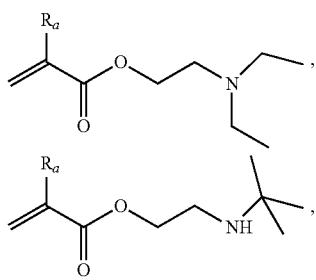

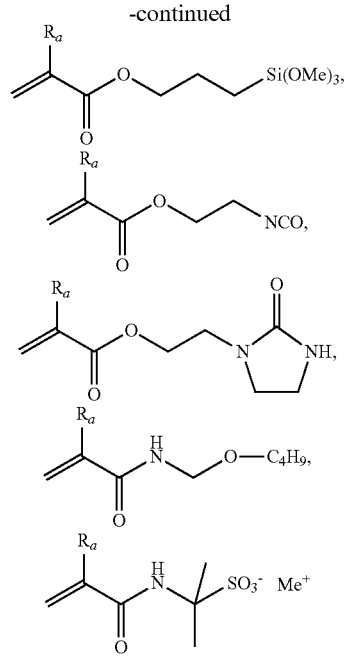

Examples for suitable monomers other than acrylates are

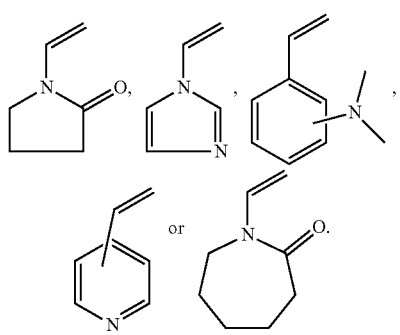

Preferably $R_a$ is hydrogen or methyl, $R_b$ is $NH_2$, glycidyl, unsubstituted or with hydroxy substituted $C_1$-$C_4$alkoxy, unsubstituted $C_1$-$C_{14}$alkylamino, di($C_1$-$C_4$alkyl)amino, hydroxy-substituted $C_1$-$C_4$alkyl-amino or hydroxy-substituted di($C_1$-$C_4$alkyl)amino; and Z is oxygen.

Acrylic acid esters and methacrylic acid esters are typically $C_1$-$C_{18}$alkyl esters.

Preferred is a concentrated aqueous polymer dispersion wherein the ethylenically unsaturated monomer is selected from the group consisting of $C_1$-$C_{18}$acrylates, $C_1$-$C_{18}$methacrylates, acrylic acid, (meth)acrylic acid, styrene, vinyltoluene, hydroxy-functional acrylates or (meth)acrylates, acrylates or (meth)acrylates derived from alkoxylated alcohols and multifunctional acrylates or (meth)acrylates or mixtures thereof.

A particularly useful methacrylate is methylmetharcrylate

In a specific embodiment the concentrated aqueous polymer dispersion is prepared from a mixture of at least two of the above monomers and at least one monomer which is bi-functional or multi-functional, so that a crosslinked polymer is obtained. The amount of bi- or multifunctional monomer is for example from 0.1 to 20 weight-%, based on the weight of the sum of monomers.

Typical examples for bi- or multi-functional monomers are divinylbenzene, ethylenglycol diacrylate, butyleneglycol diacrylate, diethyleneglycol diacrylate, trimethylolpropane triacrylate, trimethylolpropane-ethoxylate (1EO/OH)-triacrylate, glycerol-propoxylate (1PO/OH) triacrylate, pentaerythritol-propoxylate-triacrylat, pentaerythritol-triacrylate (PETIA), trimethylolpropan-triacrylate (TMPTA), pentaerythritol-tetraacrylate (PETA).

The monomers or monomer mixtures have preferably a low water solubility, which is below 5%, more preferred below 0.5% and most preferred below 0.1% by weight.

Nonionic surfactants ($c_1$) are preferably the condensation products of a $C_6$-$C_{18}$ fatty alcohol or $C_6$ to $C_{18}$ fatty acid and a mono- or disaccharide like glucose (dextrose), fructose (levulose), galactose, sucrose, lactose and maltose.

More preferred are $C_6$-$C_{18}$alkyl glucosides, like ethyl glucoside, heptyl glucoside, decyl glucoside, undecyl glucoside, octyldodecyl glucoside, C3-6 alkyl glucoside dimethicone, C6-8 alkyl glucoside, C9-C11 alkyl glucoside, C10-16 alkyl glucoside, C12-18 alkyl glucoside, C20-22 alkyl glucoside, coco-glucoside, lauryl glucoside, caprylyl glucoside, cetearyl glucoside, hydroxystearyl glucoside, isostearyl glucoside and myristyl glucoside.

Also preferred are the fatty acid glucosides like cocoyl ethyl glucoside, lauroyl ethyl glucoside; caproyl ethyl glucoside, myristoyl ethyl glucoside; oleoyl ethyl glucoside and tallowoyl ethyl glucoside.

Most preferred is lauryl glucoside, coco-glucoside, sucrose polystearate and decyl glucoside.

Anionic surfactants ($c_2$), which are preferably used in the present aqueous polymer dispersion are sulfosuccinates and sulfosuccinamates (including their salts). These compounds can best be represented as the salts of substituted sulfosuccinic acids:

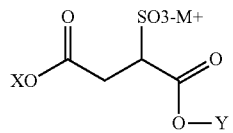

Regardless of substitution, the sulfonic acid group is always ionized, and $M^+$ represents the counterion. In compounds in which X or Y represents an alkyl or substituted alkyl group, the remaining carboxyl function is also present in salt form, (e.g., disodium deceth-6 sulfosuccinate). If both X and Y represent alkyl or substituted alkyl groupings, the sulfosuccinate is a diester, (e.g., dioctyl sodium sulfosuccinate). Fairly complex multifunctional substituents can be present on the carboxyl groups of this category. Alternately, the XO or the YO groups may be replaced by a substituted N-atom, in which case the resulting sulfosuccinamate is a monoamide (e.g., disodium stearyl sulfosuccinamate).

Examples of sulfosuccinates are ammonium dinonyl sulfosuccinate, ammonium lauryl sulfosuccinate, diammonium lauryl sulfosuccinate, diamyl sodium sulfosuccinate, dicapryl sodium sulfosuccinate, diethylhexyl sodium sulfosuccinate, diheptyl sodium sulfosuccinate, dihexyl sodium sulfosuccinate disodium cetearyl sulfosuccinate, disodium cetyl sulfosuccinate, disodium cocosulfosuccinate, disodium deceth-5 sulfosuccinate disodium deceth-6 sulfosuccinate, disodium isodecyl sulfosuccinate, disodium isostearyl sulfosuccinate, disodium laneth-5 sulfosuccinate, disodium laureth sulfosuccinate, disodium laureth-9, sulfosuccinate disodium laureth-12 sulfosuccinate, disodium lauryl sulfosuccinate, disodium oleth-3 sulfosuccinate, disodium oleyl sulfosuccinate, disodium stearyl sulfosuccinate, disodium tridecylsulfosuccinate, ditridecyl sodium sulfosuccinate or magnesium laureth-3 sulfosuccinate.

Preferably esters of succinic acid, most preferably lauryl sulfosuccinate, cetyl sulfosuccinate, stearyl sulfosuccinate or mixtures of this esters are used as anionic surfactants.

Preferred are also fatty alcoholates, most preferred is sodium cetearyl sulfate.

Also preferred anionic mixtures ($c_2$) are mixtures of phosphoric acid esters and fatty alcohols comprising from 6 to 18, preferably from 8 to 10, carbon atoms, most preferably a mixture of esters of phosphoric acid and cetyl alcohol.

Preferably, in the present invention mixtures of nonionic surfactants ($c_1$) and anionic surfactants ($c_2$) are used.

Preferred mixtures of nonionic ($c_1$) and anionic surfactants ($c_2$) are
  mixtures of C6-C18alkyl glucosides and esters of succinic acid or
  mixtures of C6-C18alkyl glucosides and mixtures of phosphoric acid esters and fatty alcohols comprising from 8 to 10, carbon atoms.

Most preferred is the mixture of nonionic ($c_1$) and anionic surfactants ($c_2$) selected from coco-glucoside and disodium lauryl sulfosuccinate.

The preparation of a concentrated aqueous polymer dispersion with an average particle size of less than 1000 nm is prepared in a manner known per se as disclosed for example in WO2005/23878, comprising the step polymerizing at least one ethylenically unsaturated monomer in the presence of an oil-soluble organic UV absorber by heterophase radical polymerization;
wherein the weight ratio of organic oil-soluble organic UV absorber to polymer carrier formed from the ethylenically unsaturated monomer is greater than 50 parts of UV absorber per 100 parts of polymer carrier.

The process for the preparation of a concentrated aqueous polymer dispersion comprises the steps
  a) dissolving, emulsifying or dispersing the oil-soluble organic UV absorber (component (b)) in at least one ethylenically unsaturated monomer;
  b) preparing a conventional oil in water emulsion of said UV absorber dissolved, emulsified or dispersed in at least one ethylenically unsaturated monomer in the presence of surfactant (c);
  c) homogenizing the conventional emulsion to a miniemulsion wherein the droplets of the organic phase have an average diameter below 1000 nm;
  d) polymerizing the miniemulsion by adding a polymerization initiator;
wherein the weight ratio of oil-soluble organic UV absorber to polymer carrier formed from the ethylenically unsaturated monomer is greater than 50 parts of UV absorber per 100 parts of polymer carrier.

Optionally other water miscible solvents may be present usually less than 10% by weight based on the water content. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof.

Preferred are water, water alcohol mixtures, water ethylene glycol or propylene glycol mixtures, water acetone, water tetrahydrofuran, or water dimethylformamide mixtures.

The homogenization step b) and c) is usually carried out by applying mechanical agitation (rotor/stator disperser) followed by using high force dispersion devices like for example an ultra-sonic sound equipment (J. Dispersion Sci. Technology 2002, 23(1-3), 333-349) or a high pressure homogenizer (APV Gaulin homogenizer; Microfluidizer) The emulsification/homogenization can be carried out continuously or batchwise. Apparatus for this purpose are known in the art. This is for example described in U.S. Pat. No. 5,108,654.

Furthermore, protective colloids such as polyvinylalcohols, starch, cellulose derivatives or copolymers containing vinylpyrrolidone may be added to form a conventional oil in water emulsion according to step b). Further examples are given in "Houben-Weyl, Methoden der Organischen Chemie, Band XIV/1, Makromolekulare Stoffe, G. Thieme Verlag Stuttgart 1961, 411-420".

The polymerization step d) is carried out by adding a free radical polymerization initiator.

Preferably the free radical initiator is present in an amount of from 0.01 weight-% to 20 weight-%, more preferably from 0.1 weight-% to 10 weight-% and most preferably from 0.2 weight-% to 5 weight-%, based on the monomer or monomer mixture.

The polymerization initiator may be added batchwise or continuously to the reaction mixture.

Preferably the free radical initiator of component b) is a bis-azo compound, a peroxide or preferably hydroperoxide.

Specific preferred radical sources are 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide) dihydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N[1,1-bis(hydroxymethyl)ethyl]propionamide} or 2,2'-azobis{2-methyl-N-[1,1-bis(hydroxymethyl)-2-hydroxyethyl]propionamide; acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis (2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)-3,5,5-trimethylcyclohexane, 1,1-bis(t-butylperoxy) cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis (t-butylperoxy) butane, 2,2 bis (t-butylperoxy) propane, dicumyl peroxide, 2,5-dimethylhexane-2,5-di-t-butylperoxide, 3-t-butylperoxy 3-phenylphthalide, di-t-amyl peroxide, bis(t-butylperoxy isopropyl) benzene, 3,5-bis (t-butylperoxy)3,5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-hydroperoxide, cumene hydroperoxide, t-butyl hydroperoxide, or most preferably hydrogen peroxide.

It is also possible to use combinations of Fe-compounds or Co-compounds with peroxo salts or salts of bisulfites or hydrosulfites. These combinations are known as redox systems.

The polymerization temperature depends on the initiator used. Usually the polymerization temperature is in the range of 20 and 80° C. Polymerization under normal pressure is the usual process.

Alternatively, the polymerization can be initiated by photoinitiators and electromagnetic radiation, in particular actinic radiation.

Photoinitiators suitable for use in the process according to the invention are in principle any compounds and mixtures that form one or more free radicals when irradiated with electromagnetic waves. These include initiator systems consisting of a plurality of initiators and systems that function independently of one another or synergistically. In addition to coinitiators, for example amines, thiols, borates, enolates, phosphines, carboxylates and imidazoles, it is also possible to use sensitisers, for example acridines, xanthenes, thiazenes, coumarins, thioxanthones, triazines and dyes. A description of such compounds and initiator systems can be found e.g. in Crivello J. V., Dietliker K. K., (1999): Chemistry & Technology of UV & EB Formulation for Coatings, Inks & Paints, and in Bradley G. (ed.) Vol. 3: Photoinitiators for Free Radical and Cationic Polymerisation 2nd Edition, John Wiley & Son Ltd. The photoinitiator suitable for the process according to the invention in step b) may be either an initiator having an unsaturated group or an initiator not having such a group.

Such compounds and derivatives are derived, for example, from the following classes of compounds: benzoins, benzil ketals, acetophenones, hydroxyalkylphenones, aminoalkylphenones, acylphosphine oxides, acylphosphine sulfides, acyloxyiminoketones, alkylamino-substituted ketones, such as Michleram ketone, peroxy compounds, dinitrile compounds, halogenated acetophenones, phenylglyoxylates, dimeric phenylglyoxalates, benzophenones, oximes and oxime esters, thioxanthones, coumarins, ferrocenes, titanocenes, onium salts, sulfonium salts, iodonium salts, diazonium salts, borates, triazines, bisimidazoles, polysilanes and dyes. It is also possible to use combinations of the compounds from the mentioned classes of compounds with one another and combinations with corresponding coinitiator systems and/or sensitisers.

The pH adjustment of the final dispersion can be carried out with the methods known to the skilled persons by adding water soluble alkylamines, hydroxylakylamines, amino acids, ammonia, alkali hydroxides or alkali carbonates.

Preferred pH ranges are from 6 to 12, more preferred from 8 to 11 and most preferred from 9.5 to 10.5 for storage stability reasons and protection against growth of microorganisms.

Alternatively, biocides can be added at the end of the polymerization

After polymerization has been completed, the volatile components, water mainly, can be removed without agglomeration of the particles. The polymer particles can therefore readily be redispersed, if desired.

Vaporization of the volatile components can be carried out using standard methods, such as for example spray drying.

Another aspect of the present invention is a cosmetic composition, which comprises, (A) an aqueous polymer dispersion according to claim 1; and
(B) a cosmetically acceptable carrier; and optionally
(C) ethanol.

The cosmetic composition according to the present invention is preferably used for preventing the human hair or skin from the harmful effect of UV radiation.

The cosmetic composition may preferably used
in aqueous environments/media/formulations;
for the improvement of the sun protection factor (SPF);
for increasing the amount of UV filters in the water phase, thus reducing the overall concentration of UV filters in sunscreen formulations maintaining the same performance; and
for the improvement of the water resistance.

It has been shown that cosmetic compositions containing the aqueous polymer dispersion of the invention show excellent performance in anti-pollen efficacy.

The present invention is also directed on the use of the aqueous polymer dispersion of the invention in cosmetic compositions to prevent pollen from attaching to the skin.

Further, the cosmetic compositions containing the aqueous polymer dispersion of the invention surprisingly provide an anti-oxidation effect on the skin, specifically the sebum.

Thus, the present also describes the use of the aqueous polymer dispersion of the invention in cosmetic compositions to avoid damages on the skin caused by UV light.

In addition, the cosmetic compositions containing the aqueous polymer dispersion of the invention have an excellent performance in reducing particle (i.e. dust, sand, pollen) adhesiveness on the skin. Therefore, cosmetic compositions comprising the aqueous polymer dispersion of the invention can be perfectly used in dusty and sandy environments such as on the beach and in cities.

The cosmetic or pharmaceutical preparations may be, for example, creams, gels, lotions, alcoholic and aqueous/alcoholic solutions, emulsions, wax/fat compositions, stick preparations, powders or ointments.

In a preferred embodiment of the present invention the cosmetic composition according to the present invention represents a spray formulation. This spray formulation contains (C) ethanol in amounts from 0.1 to 10% by weigh of the cosmetic composition. Spray formulations stay liquid and the ethanol tolerance is increased.

In addition, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or more additional compounds as like fatty alcohols, esters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, adjuvants and additives, super-fatting agents, surfactants, consistency regulators/thickeners and rheology modifiers, polymers, biogenic active ingredients, deodorising active ingredients, anti-dandruff agents, antioxidants, hydrotropic agents, preservatives, bacteriainhibiting agents, perfume oils, colourants, polymeric beads or hollow spheres as SPF enhancers.

Cosmetic or Pharmaceutical Preparations

Cosmetic or pharmaceutical formulations are contained in a wide variety of cosmetic preparations. There come into consideration, for example, especially the following preparations: skin-care preparations, bath preparations, cosmetic personal care preparations, foot-care preparations, light-protective preparations, skin-tanning preparations, depigmenting preparations, insect-repellents, deodorants, antiperspirants, preparations for cleansing and caring for blemished skin, hair-removal preparations in chemical form (depilation), shaving preparations, fragrance preparations, cosmetic hair-treatment preparations.

Presentation Forms

The final formulations listed may exist in a wide variety of presentation forms, for example:
in the form of liquid preparations as a W/O, O/W, O/W/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellant gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or aftersun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic preparation according to the invention is distinguished by excellent protection of human skin against the damaging effect of sunlight.

The following examples illustrate the invention.

A. PREPARATION EXAMPLES

Example A1

For the preparation of a stable oil/water emulsion 100 g of the compound (101)

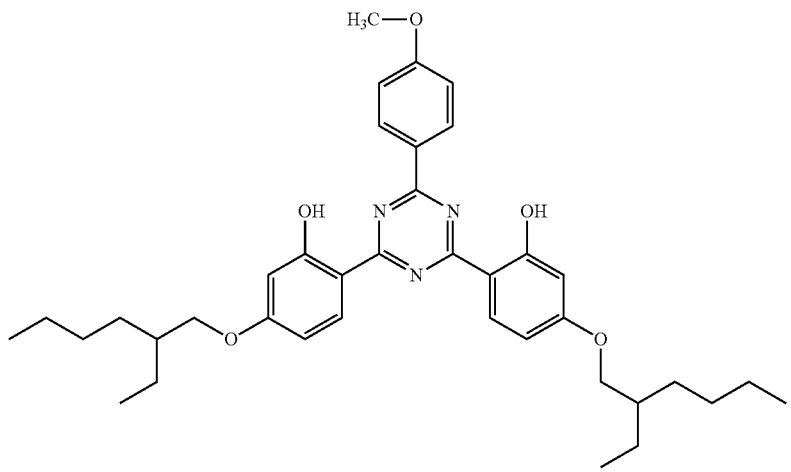 [SMILES: CCCCC(CC)COc1ccc(-c2nc(-c3ccc(OC)cc3)nc(-c3ccc(OCC(CC)CCCC)cc3O)n2)c(O)c1]

are dissolved in 90 g of methyl methacrylate (MMA), 8 g stearyl methacrylate (SMA), 2 g methacrylic acid (MAA) and 0.30 g of butandioldiacrylate (BDDA) at 45° C. The oil phase is added dropwise to a stirred solution of 26.8 g of a mixture of coco-glucoside, disodium lauryl sulfosuccinate and glycerol (Plantapon® PSC) (56 wt % active, BASF SE) in 230 g of deionised water.

After stirring for 30 min and ultrasound conversion a stable emulsion is obtained with an average droplet size below 200 nm.

The emulsion is heated up to 45° C. and 7.5 g of $H_2O_2$ (4%) and 20.5 g of ascorbic acid solution (3.9%) are subsequently added to the reaction mixture. The reaction mixture is continuously stirred by a mechanical stirrer and maintained at 55° C. for 3 h, then cooled to RT and 15 g L-arginine are added, then and filtered via a 20 μm filter.

The resulting particle size $D_{50}$ is 165 nm.

The active content of the oil soluble UV absorber compound is 20 wt %, based on the total weight of the final dispersion.

The solid content of the dispersion is 45.6% (Halogendryer HR73 Mettler Toledo at 150° C.). The pH of the dispersion is 10.2.

Example A2

For the preparation of a stable oil/water emulsion 80 g of the compound (101) are dissolved in 72 g methyl methacrylate (MMA), 6.4 g stearyl methacrylate (SMA), 1.6 g methacrylic acid (MAA) and 0.24 g pentaerythritol triacrylate (PETIA) at 35° C. 12.44 g lauryl glucoside (Plantacare® 1200UP) (51 wt % active, BASF SE), 2.15 g Plantacare® 810UP (62 wt % active, BASF SE) and 2.28 g disodium lauryl sulfosuccinate (Plantapon® SUS) (100% active, BASF SE) are added to the oil phase and homogenized. Then 189 g of deionized water are slowly added under stirring. After stirring for 30 min and ultrasound conversion a stable emulsion is obtained with an average droplet size below 200 nm.

The emulsion is heated up to 45° C. and 6 g of $H_2O_2$ (4%) are added. Then 16.4 g ascorbic acid solution (3.9%) are dosed over a period of 1 h. The reaction mixture is continuously stirred by a mechanical stirrer and is maintained at 60-65° C. for 1 h, then cooled to RT, 1.5 g of Aminomethylpropanol (AMP-90) are added, and finally filtered via a 20 μm filter.

The resulting particle size $D_{50}$ is 144 nm.

The active content of the oil soluble UV absorber compound is 20 wt %, based on the total weight of the final dispersion.

The solid content of the dispersion is 43.2% (Halogendryer HR73 Mettler Toledo at 150° C.).

The pH of the dispersion is 9.8.

Example A3

For the preparation of a stable oil/water emulsion a solution of 26.8 g of a mixture of coco-glucoside, disodium lauryl sulfosuccinate and glycerol (Plantapon® PSC) (56 wt % active, BASF SE) in 230 g deionized water is slowly added to a solution of 100 g of the compound (101), dissolved in 89 g methyl methacrylate (MMA), 8 g stearyl methacrylate (SMA), 2 g methacrylic acid (MAA) and 1 g hexanedioldiacrylate (HDDA) at 40° C. After stirring for 30 min and conversion by APV homogenizer at 600 bar a stable emulsion is obtained with an average droplet size below 200 nm.

The emulsion is heated up to 40° C. and 7.5 g of $H_2O_2$ (4%) and 20.5 g ascorbic acid solution (3.9%) are subsequently added to the reaction mixture. The reaction mixture is continuously stirred by a mechanical stirrer and maintained at 60° C. for 1 h, then cooled to RT and 15 g L-arginine are added, and finally filtered via a 20 μm filter.

The resulting particle size $D_{50}$ is 136 nm.

The active content of the oil soluble UV absorber compound is 20 wt %, based on the total weight of the final dispersion.

The solid content of the dispersion is 44.7% (Halogendryer HR73 Mettler Toledo at 150° C.).

The pH of the dispersion is 10.1.

Example A4

For the preparation of a stable oil/water emulsion 68.6 g of the compound (101) are dissolved in 58.7 g methyl methacrylate (MMA), 5.2 g stearyl methacrylate (SMA), 1.3 g methacrylic acid (MAA) and 0.2 g butandioldiacrylate (BDDA) at 35° C. 8.03 g decyl glucoside (Plantacare® 2000UP) (50 wt % active, BASF SE), and 3.12 g potassium cetyl phosphate (Amphisol K) (50 wt % active, DSM) are added to the oil phase and homogenized. Then 160 g deionised water are slowly added under stirring. After stirring for 30 min and ultrasound conversion a stable emulsion is obtained with an average droplet size below 200 nm.

The emulsion is heated up to 45° C. and 4.9 g $H_2O_2$ (4%) are added. Then 13.4 g ascorbic acid solution (3.9%) are dosed over a period of 1 h. The reaction mixture is continuously stirred by a mechanical stirrer and maintained at 70° C. for 1 h, then cooled to RT and 1.2 g of AMP-90 are added, and finally filtered via a 20 μm filter.

The resulting particle size $D_{50}$ is 164 nm.

The active content of the oil soluble UV absorber compound is 20 wt %, based on the total weight of the final dispersion.

The solid content of the dispersion is 42.0% (Halogendryer HR73 Mettler Toledo at 150° C.).

The pH of the dispersion is 9.9.

Example A5

For the preparation of a stable oil/water emulsion 80 g of the compound (101) are dissolved in 72 g methyl methacrylate (MMA), 6.4 g behenylacrylate (BhA), 1.6 g methacrylic acid (MAA) and 0.24 g butandioldiacrylate (BDDA) at 35° C. 7.8 g lauryl glucoside (Plantacare® 1200UP) (51 wt % active, BASF SE) and 2.0 g sodium cetearyl sulfate (Lanette® E) (100 wt % active, BASF) are added to the oil phase and homogenized. Then 188 g deionised water are slowly added under stirring. After stirring for 30 min and ultrasound conversion a stable emulsion is obtained with an average droplet size below 200 nm.

The emulsion is heated up to 40° C. and 5.95 g of $H_2O_2$ (4%) are added. Then 16.4 g ascorbic acid solution (3.9%) are dosed over a period of 1 h. The reaction mixture is continuously stirred by a mechanical stirrer and is maintained at 60-65° C. for 1 h, then cooled to RT and 1.6 g of AMP-Ultra PC 3000 are added, and finally filtered via a 20 μm filter.

The resulting particle size $D_{50}$ is 192 nm.

The active content of the oil soluble UV absorber compound is 20 wt %, based on the total weight of the final dispersion.

The solid content of the dispersion is 41.0% (Halogendryer HR73 Mettler Toledo at 150° C.).

The pH of the dispersion is 10.0.

Example A6

For the preparation of a stable oil/water emulsion 80 g of the compound (101) are dissolved in 72 g of methyl methacrylate (MMA), 6.4 g stearyl methacrylate (SMA), 1.6 g methacrylic acid (MAA) and 0.24 g butandioldiacrylate (BDDA) at 40° C. and a suspension of 2.0 g disodium cetearyl sulfosuccinate (Eumulgin® Prisma) (100 wt % active, BASF SE) and a mixture of sucrose polystearate and hydrogenated polyisobutene (Emulgade® Sucro) (80% active, BASF SE) in 210 g deionised water are added. After stirring for 30 min and ultrasound conversion a stable emulsion is obtained with an average droplet size below 200 nm.

The emulsion is heated up to 45° C. and 6.0 g $H_2O_2$ 4%) and 16.4 g ascorbic acid solution (3.9%) are subsequently added to the reaction mixture. The reaction mixture is continuously stirred by a mechanical stirrer and maintained at 60-65° C. for 1 h, then cooled to RT and 2.4 g AMP Ultra PC 3000 are added and finally filtered via a 20 μm filter.

The resulting particle size $D_{50}$ is 230 μm.

The active content of the oil soluble UV absorber compound is 20 wt %, based on the total weight of the final dispersion.

The solid content of the dispersion is 40.6% (Halogendryer HR73 Mettler Toledo at 150° C.).

The pH of the dispersion is 9.9.

Example A7

For the preparation of a stable oil/water emulsion a solution of 15.0 g of sodium cocoamphoacetate (Dehyton® MC) (40 wt % active, BASF SE) in 202 g of deionised water is slowly added to a solution of 100 g of the compound (101), dissolved in 80 g methyl methacrylate (MMA), 6.4 g lauryl methacrylate (LMA), 1.6 g of methacrylic acid (MAA) and 0.25 g butandioldiacrylate (BDDA) at 40° C. After stirring for 30 min and conversion by APV homogenizer at 400 bar, a stable emulsion is obtained with an average droplet size below 250 nm.

The emulsion is heated up to 40° C. and 6.0 g of $H_2O_2$ (4%) and 16.4 g ascorbic acid solution (3.9%) are subsequently added to the reaction mixture. The reaction mixture is continuously stirred by a mechanical stirrer and is maintained at 60-65° C. for 1 h, then cooled to RT and 1.5 g of AMP90 are added, and finally filtered via a 20 μm filter.

The resulting particle size $D_{50}$ is 310 nm.

The active content of the oil soluble UV absorber compound is 20 wt %, based on the total weight of the final dispersion.

The solid content of the dispersion is 42.1% (Halogendryer HR73 Mettler Toledo at 150° C.)

The pH of the dispersion is 9.8.

Example A8

For the preparation of a stable oil/water emulsion 300 g of the compound (101) are dissolved in 270 g methyl methacrylate (MMA), 24 g stearyl methacrylate (SMA), 6 g methacrylic acid (MAA) and 0.90 g of butandioldiacrylate (BDDA) at 35° C. 22.5 g disodium lauryl sulfosuccinate (Plantapon® SUS) (100 wt % active, BASF SE) are added to the oil phase and homogenized. Then 793 g deionised water are slowly added under stirring. After stirring for 30 min and conversion by APV homogenizer at 600 bar, a stable emulsion is obtained with an average droplet size below 200 nm. The emulsion is heated up to 45° C. and 22.3 g of $H_2O_2$ (4%) are added. Then 61.6 g ascorbic acid solution (3.9%) are dosed over a period of 1 h. The reaction mixture is continuously stirred by a mechanical stirrer and maintained at 60-65° C. for 1 h, then cooled to RT and 5.2 g of AMP-90 are added and filtered via a 20 μm filter. The resulting particle size $D_{50}$ is 150 nm.

The active content of the oil soluble UV absorber compound is 20 wt %, based on the total weight of the final dispersion.

The solid content of the dispersion is 39.% (Halogendryer HR73 Mettler Toledo at 150° C.).

The pH of the dispersion is 9.9.

Example A9

For the preparation of a stable oil/water emulsion 68.6 g of the compound (101) are dissolved in 29 g methyl methacrylate (MMA), 29 g n-butylacrylate (nBA), 5.2 g stearyl methacrylate (SMA), 1.3 g methacrylic acid (MAA) and 0.2 g butandioldiacrylate (BDDA) at 35° C. 8.03 g decyl glucoside (Plantacare® 2000UP) (50 wt % active, BASF SE), and 3.12 g of Amphisol K (50 wt % active, DSM) are added to the oil phase and homogenized. Then 160 g deionised water are slowly added under stirring. After stirring for 30 min and ultrasound conversion a stable emulsion is obtained with an average droplet size below 200 nm.

The emulsion is heated up to 45° C. and 4.9 g of $H_2O_2$ (4%) are added. Then 13.4 g of ascorbic acid solution (3.9%) are dosed over a period of 1 h. The reaction mixture is continuously stirred by a mechanical stirrer and maintained at 70° C. for 1 h, then cooled to RT and 1.2 g of AMP-90 are added, and finally filtered via a 20 µm filter.

The resulting particle size $D_{50}$ is 185 nm.

The active content of the oil soluble UV absorber compound is 20 wt %, based on the total weight of the final dispersion.

The solid content of the dispersion is 41.5% (Halogendryer HR73 Mettler Toledo at 150° C.).

The pH of the dispersion is 9.8.

Example A10

For the preparation of a stable oil/water emulsion 80 g of the compound (101), dissolved in 72 g methyl methacrylate (MMA), 6.4 g stearyl methacrylate (SMA), 0.5 g acetic acid and 0.25 g of butandioldiacrylate (BDDA) at 40° C. are slowly added to a solution of 35.0 g sodium cocoamphoacetate (Dehyton® MC) (40 wt % active, BASF SE) in 182 g of deionised water. After stirring for 30 min and ultrasound treatment a stable emulsion is obtained with an average droplet size below 200 nm.

The emulsion is heated up to 45° C. and 6.0 g of $H_2O_2$ (4%) and 16.4 g of ascorbic acid solution (3.9%) are subsequently added to the reaction mixture. The reaction mixture is continuously stirred by a mechanical stirrer and is maintained at 60° C. for 1 h, then cooled to RT and 30 g of $Na_2CO_3$ solution (20%) are added, and finally filtered via a 20 µm filter.

The resulting particle size $D_{50}$ is 157 nm.

The active content of the oil soluble UV absorber compound is 20 wt %, based on the total weight of the final dispersion. The solid content of the dispersion is 41.7% (Halogendryer HR73 Mettler Toledo at 150° C.), the pH of the dispersion is 10.3.

Example A11

For the preparation of a stable oil/water emulsion 100 g of the compound (101) are dissolved in 90 g of methyl methacrylate (MMA), 8 g stearyl methacrylate (SMA), 2 g methacrylic acid (MAA) and 0.30 g of butandioldiacrylate (BDDA) at 45° C. The oil phase is added dropwise to a stirred solution of a mixture of 18.6 g of coco-glucoside (Plantacare® 1200 UP and Plantacare 810 UP) (50 wt % active, BASF SE), and 3.1 g disodium lauryl sulfosuccinate (Plantapon® SUS, BASF SE) in 235 g of deionised water. After stirring for 30 min and ultrasound conversion a stable emulsion is obtained with an average droplet size below 200 nm.

The emulsion is heated up to 45° C. and 7.5 g of $H_2O_2$ (4%) and 20.5 g of ascorbic acid solution (3.9%) are subsequently added to the reaction mixture. The reaction mixture is continuously stirred by a mechanical stirrer and maintained at 55° C. for 3 h, then cooled to RT and 15 g L-arginine are added, then and filtered via a 20 µm filter.

The resulting particle size $D_{50}$ is 163 nm.

The active content of the oil soluble UV absorber compound is 20 wt %, based on the total weight of the final dispersion.

The solid content of the dispersion is 44.15% (Halogendryer HR73 Mettler Toledo at 150° C.).

The pH of the dispersion is 10.1.

Example A12

For the preparation of a stable oil/water emulsion 100 g of the compound (101) are dissolved in 90 g of methyl methacrylate (MMA), 8 g stearyl methacrylate (SMA), 2 g methacrylic acid (MAA) and 0.30 g of butandioldiacrylate (BDDA) at 45° C. The oil phase is added dropwise to a stirred solution of a mixture of 18.8 g of decyl glucoside (Plantacare® 2000UP) (50 wt % active, BASF SE) and 2.9 g disodium lauryl sulfosuccinate (Plantapon® SUS, BASF SE) in 235 g of deionised water. After stirring for 30 min and ultrasound conversion a stable emulsion is obtained with an average droplet size below 200 nm.

The emulsion is heated up to 45° C. and 7.5 g of $H_2O_2$ (4%) and 20.5 g of ascorbic acid solution (3.9%) are subsequently added to the reaction mixture. The reaction mixture is continuously stirred by a mechanical stirrer and maintained at 55° C. for 3 h, then cooled to RT and 15 g L-arginine are added, then and filtered via a 20 µm filter.

The resulting particle size $D_{50}$ is 176 nm.

The active content of the oil soluble UV absorber compound is 20 wt %, based on the total weight of the final dispersion.

The solid content of the dispersion is 44.64% (Halogendryer HR73 Mettler Toledo at 150° C.).

The pH of the dispersion is 10.1.

Example A13

For the preparation of a stable oil/water emulsion 100 g of the compound (101) are dissolved in 90 g of methyl methacrylate (MMA), 8 g stearyl methacrylate (SMA), 2 g methacrylic acid (MAA) and 0.30 g of butandioldiacrylate (BDDA) at 45° C. The oil phase is added dropwise to a stirred solution of a mixture of 18.6 g of coco-glucoside (Plantacare® 1200 UP and Plantacare 810 UP) (50 wt % active, BASF SE), and 3.1 g disodium lauryl sulfosuccinate (Plantapon® SUS, BASF SE) in 233.6 g of deionised water. After stirring for 30 min and ultrasound conversion a stable emulsion is obtained with an average droplet size below 200 nm.

The emulsion is heated up to 45° C. and 7.5 g of $H_2O_2$ (4%) and 20.5 g of ascorbic acid solution (3.9%) are subsequently added to the reaction mixture. The reaction mixture is continuously stirred by a mechanical stirrer and maintained at 55° C. for 3 h, then cooled to RT and 1.4 g disodium lauryl sulfosuccinate (Plantapon® SUS, BASF SE) and 15 g L-arginine are added under stirring until dissolved, and then filtered via a 20 µm filter.

The resulting particle size $D_{50}$ is 176 nm.

The active content of the oil soluble UV absorber compound is 20 wt %, based on the total weight of the final dispersion.

The solid content of the dispersion is 45.00% (Halogendryer HR73 Mettler Toledo at 150° C.).

The pH of the dispersion is 10.0.

The dispersions produced in Examples A1 to A13 have acquired the INCI name Aqua (and) Bis-Ethylhexyloxyphenol Methoxyphenyl Triazine (and) Acrylates/C12-22 Alkyl Methacrylate Copolymer and the product thereof is available as Tinosorb® S Lite Aqua.

B. APPLICATION EXAMPLES

Formulation B1: Spray, SPF 30

|   | Tradename | INCI-Name | Amount % w/w (as supplied) B1-1 | B1-2 |
|---|---|---|---|---|
| A | Eumulgin ® SG | Sodium Stearoyl Glutamate | 2.00 | 2.00 |
|   | Cetiol ® AB | C12-15 Alkyl Benzoate | 2.00 | 2.00 |
|   | Cetiol ® B | Dibutyl Adipate | 2.00 | 2.00 |
|   | Cetiol ® SN | Cetearyl Isononanoate | 2.00 | 2.00 |
|   | Dermosoft ® Octiol | Caprylyl Glycol | 0.40 | 0.40 |
|   | Uvinul ® N539T | OCR | 10.00 | 10.00 |
|   | Neoheliopan ® OS | EHS | 5.00 | 5.00 |
|   | Parsol ® 1789 | BMDBM | 5.00 | 5.00 |
|   | Uvinul ® A Plus | Diethylamino Hydroxybenzoyl Hexyl Benzoate | 4.90 | 4.90 |
|   | Tinosorb ® S | BEMT | 1.00 | 1.00 |
| B | Water | Aqua | 35.80 | 35.80 |
|   | Edeta ® BD | Disodium EDTA | 0.20 | 0.20 |
|   | Pemulen ® TR-2 | Acrylates/C10-30 Alkyl Acrylate Crosspolymer | 0.10 | 0.10 |
|   | Rheocare ® TTA | Acrylates Copolymer | 0.50 | 0.50 |
| C | Eusolex ® 232 | Phenylbenzimidazole Sulfonic Acid | 0.50 | 0.50 |
|   | Water | water | 5.00 | 5.00 |
|   | Tris-amino ultra pure | Tromethamine | 0.40 | 0.40 |
| D | Tinosorb ® S Aqua | Aqua (and) Bis-Ethylhexyloxyphenol Methoxyphenyl Triazine (and) Polymethyl Methacrylate | 10.00 | |
|   | Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 |
|   | Cetiol ® Ultimate | Cyclohexasiloxane (and) Cyclopentasiloxane | 5.00 | 5.00 |
|   | Ethanol | | 8.00 | 8.00 |

Consistency of the formulations was evaluated after preparation (start) as well as after 3 months of storage at different temperatures (4° C., RT, 40° C.).

The samples are applied on sand blasted PMMA plates (delivered by Helioscience, Marseille, France) with a concentration of 1.4 mg/cm², irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | Formulation B1-1 with Tinosorb S Aqua | Formulation B1-2 with Tinosorb S Lite Aqua |
|---|---|---|
| pH | 7.67 | 7.76 |
| consistency Start | highly fluid | highly fluid |
| consistency 3 mon RT | fluid | highly fluid |
| consistency 3 mon 40° C. | firm | highly fluid |
| consistency 3 mon 4° C. | fluid | highly fluid |
| Viscosity DVIII + LV/Sp2 + 3/10 rpm n. 1 d | 1356 mPa s | 438 mPa s |
| Viscosity DVIII + LV/SP3/10 rpm n. 3 mon | 5035 mPa s | 852 mPa s |
| reached SPF (Sun Protection Factor) for labeling | 30 | 30 |

The formulation with Example B1-2 according to the present invention is stable up to 3 months whereas the state of the art formulation B1-1 could not be used any more after storage.

Formulation B2: Spray, SPF 30

|   | Tradename | INCI-Name | Amount % w/w (as supplied) B2-1 | B2-2 |
|---|---|---|---|---|
| A | Eumulgin ® SG | Sodium Stearoyl Glutamate | 2.00 | 2.00 |
|   | Cetiol ® AB | C12-15 Alkyl Benzoate | 2.00 | 2.00 |
|   | Cetiol ® B | Dibutyl Adipate | 2.00 | 2.00 |
|   | Cetiol ® SN | Cetearyl Isononanoate | 2.00 | 2.00 |

| Formulation B2: Spray, SPF 30 | | | | |
|---|---|---|---|---|
| | | | Amount % w/w (as supplied) | |
| | Tradename | INCI-Name | B2-1 | B2-2 |
| | Dermosoft ® Octiol | Caprylyl Glycol | 0.40 | 0.40 |
| | Uvinul ® N539T | OCR | 10.00 | 10.00 |
| | Neoheliopan ® OS | EHS | 5.00 | 5.00 |
| | Parsol ® 1789 | BMDBM | 5.00 | 5.00 |
| | Uvinul ® A Plus | Diethylamino Hydroxybenzoyl Hexyl Benzoate | 4.90 | 4.90 |
| | Tinosorb ® S | BEMT | 1.00 | 1.00 |
| B | Water | Aqua | 33.80 | 33.80 |
| | Edeta ® BD | Disodium EDTA | 0.20 | 0.20 |
| | Pemulen ® TR-2 | Acrylates/C10-30 Alkyl Acrylate Crosspolymer | 0.10 | 0.10 |
| | Rheocare ® TTA | Acrylates Copolymer | 0.50 | 0.50 |
| C | Eusolex ® 232 | Phenylbenzimidazole Sulfonic Acid | 0.50 | 0.50 |
| | Water | water | 5.00 | 5.00 |
| | Tris-amino ultra pure | Tromethamine | 0.40 | 0.40 |
| D | Tinosorb ® S Aqua | Aqua (and) Bis-Ethylhexyloxyphenol Methoxyphenyl Triazine (and) Polymethyl Methacrylate | 10.00 | |
| | Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 |
| | Cetiol ® Ultimate | Cyclohexasiloxane (and) Cyclopentasiloxane | 5.00 | 5.00 |
| E | Ethanol | Ethanol | 10.00 | 10.00 |

The viscosity of the formulations was determined.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | Formulation B2-1 with Tinosorb S Aqua | Formulation B2-2 with Tinosorb S Lite Aqua |
|---|---|---|
| pH | 8.04 | 8.06 |
| Viscosity DVIII + LV/Sp2 + 3/10 rpm n. 1 d | 2692 | 444 |
| Viscosity DVIII + LV/SP3/10 rpm n. 3 mon | Lump formation, no measurement possible | 633 |
| Calculated in silico SPF (Sun Protection Factor) | 30 | 30 |
| reached SPF (Sun Protection Factor) for labeling | Lump formation, no measurement possible | 50 |

The formulation B2-2 according to the present invention shows unexpected high SPF compared to calculated values as well as high tolerance against ethanol compared to state of the art formulation B2-1, which is not stable in the presence of ethanol.

| Formulation B3: W/O SPF 25 | | | |
|---|---|---|---|
| | | Amount % w/w (as supplied) | |
| Tradename | INCI-Name | B3-1 | B3-2 |
| Eumulgin ® Prisma | Disodium Cetearyl Sulfosuccinate | 0.30 | 0.30 |
| Cetiol ® C5 | Coco-Caprylate | 4.00 | 4.00 |
| Uvinul ® A Plus | Diethylamino Hydroxybenzoyl Hexyl Benzoate | 4.00 | 4.00 |
| Uvinul ® MC 80 | Ethylhexyl Methoxycinnamate | 8.00 | 8.00 |
| Water | Aqua | Add 100 | Add 100 |
| Luvigel ® EM | Caprylic/Capric Triglycerid (and) Sodium Acrylates Copolymer | 3 | 3 |

-continued

| Formulation B3: W/O SPF 25 | | | |
|---|---|---|---|
| | | Amount % w/w (as supplied) | |
| Tradename | INCI-Name | B3-1 | B3-2 |
| Tinosorb ® S Aqua | Aqua (and) Bis-Ethylhexyloxyphenol Methoxyphenyl Triazine (and) Polymethyl Methacrylate | 10 | |
| Tinosorb ® S Lite Aqua | Aqua (and) Bis-Ethylhexyloxyphenol Methoxyphenyl Triazine (and) Acrylates/C12-22 Alkyl Methacrylate Copolymer | | 10 |
| Protectol ® PE | Phenoxyethanol | 1 | 1 |
| Parfume | | 1 | 1 |

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | | |
|---|---|---|
| | Formulation B3-1 with Tinosorb S Aqua | Formulation B3-2 with Tinosorb S Lite Aqua |
| pH | 6.25 | 6.02 |
| Viscosity DVIII + RV6/10 rpm | 16000 mPa s | 16600 mPa s |
| SPF in silico (real life rating) | 25 | 25 |
| SPF in vitro Start | 23 | 29 |
| SPF in vitro 3 mon RT | 26 | 29 |
| SPF in vitro 3 mon 40° C. | 29 | 32 |

Formulation B3-2 according to the present invention shows higher SPF values even after storage compared to B3-1 formulation.

| Formulation B4: Shake Well SPF 50 | | |
|---|---|---|
| | | Amount % w/w (as supplied) |
| Tradename | INCI-Name | B4 |
| A Cetiol ® B | Dibutyl Adipate | 8.00 |
| DUB DIS | Diisopropyl Sebacate | 6.00 |
| Uvinul ® MC80 | Ethylhexyl Methoxycinnamate | 10.00 |
| Uvinul ® A Plus | Diethylamino Hydroxybenzoyl Hexyl Benzoate | 9.00 |
| Uvinul ® T 150 | Ethylhexyl Triazone | 1.00 |
| Tinosorb ® S | Bis-Ethylhexyloxyphenol Methoxyphenyl Triazine | 0.50 |
| B Demin. Wasser | Aqua | 22.30 |
| Tinosorb ® S Lite Aqua | Aqua (and) Bis-Ethylhexyloxyphenol Methoxyphenyl Triazine (and) Acrlates/C12-22 Alkyl Methacrylate Copolymer | 5.00 |
| Butylene Glycol | Butylene Glycol | 3.00 |
| Sodium Chloride | Sodium Chloride | 1.00 |
| Edeta ® BD | Disodium EDTA | 0.20 |
| Xiameter PMX-200 Silicon Fluid 1CS | Dimethicone | 22.00 |
| Ethanol | Alcohol | 8.00 |

The samples are applied on sand blasted PMMA plates (delivered by Helioscience, Marseille, France) with a concentration of 1.4 mg/cm² M irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | Formulation B4 with Tinosorb S Lite Aqua |
|---|---|
| pH | 7.15 |
| consistency | fluid |
| Calculated in silico SPF | 50 |
| reached SPF (Sun Protection Factor) for labeling | 50+ |

The formulation B4 according to the present invention shows a higher sun protection factor (SPF) than calculated and expected.

| Formulation B5: Spray, SPF 30 ||||
|---|---|---|---|
| | Tradename | INCI-Name | Amount % w/w (as supplied) B5 |
| A | Cetiol ® C5 | Coco-Caprylate | 4.00 |
| | Cetiol ® B | Dibutyl Adipate | 3.50 |
| | Uvinul ® A Plus B | Ethylhexyl Methoxycinnamate and Diethylamino Hydroxybenzoyl Hexyl Benzoate | 15.00 |
| | Euxyl ® PE 9010 | Phenoxyethanol | 1.00 |
| B | Demin. Wasser | Aqua | 67.35 |
| | Eumulgin ® SG | Sodium Stearoyl Glutamate | 1.00 |
| | Keltrol ® CG-RD | Xanthan Gum | 0.10 |
| | Edeta ® BD | Disodium EDTA | 0.05 |
| | Tinovis ® GTC UP | Acrylates/Beheneth-25 Methacrylate Copolymer | 0.70 |
| C | Tinosorb ® S Lite Aqua | Aqua (and) Bis-Ethylhexyloxyphenol Methoxyphenyl Triazine (and) Acrylates/C12-22 Alkyl Methacrylate Copolymer | 5.00 |
| | Cetiol ® Ultimate | Undecane, Tridecane | 2.00 |
| | Citric Acid 30% | Citric Acid | 0.30 |

The samples are applied on sand blasted PMMA plates (delivered by Helioscience, Marseille, France) with a concentration of 1.4 mg/cm², irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | Formulation B5 with Tinosorb S Lite Aqua |
|---|---|
| pH | 6.53 |
| consistency | fluid |
| Viskosität DVIII + RV6/10 rpm | 3757 mPa s |
| in vitro SPF (Sun Protection Factor) | 39 |

The sun protection spray formulation B5 according to the present invention shows higher SPF than calculated and expected.

| | Formulation B6: O/W, SPF 50 | | |
|---|---|---|---|
| | Tradename | INCI-Name | Amount % s/w (as supplied) B6 |
| A | Eumulgin ® Prisma | Disodium Cetearyl Sulfosuccinate | 2.00 |
| | Lanette ® O | Cetearyl Alcohol | 1.00 |
| | Cetiol ® B | Dibutyl Adipate | 8.00 |
| | Dermofeel ® TC-7 | Triheptanoin | 3.00 |
| | Uvinul ® A Plus | Diethylamino Hydroxybenzoyl Hexyl Benzoate | 10.00 |
| | Uvinul ® MC80 | Ethylhexyl Methoxycinnamate | 6.00 |
| | Uvinul ® T150 | Ethylhexyl Triazone | 2.70 |
| | Tinosorb ® S | Bis-Ethylhexyloxyphenol Methoxyphenyl Triazine | 1.00 |
| B | Demin. Wasser | Aqua | 47.20 |
| | Tinosorb ® S Lite Aqua | Aqua (and) Bis-Ethylhexyloxyphenol Methoxyphenyl Triazine (and) Acrylates/C12-22 Alkyl Methacrylate Copolymer | 10.00 |
| | Butylen Glycol | Butylene Glycol | 2.00 |
| | Keltrol ® CG-T | Xanthan Gum | 0.50 |
| | Edeta ® BD | Disodium EDTA | 0.20 |
| D | Tinovis ® ADE | Sodium Acrylates Copolymer, Hydrogenated Polydecene, PPG-1 Trideceth-6 | 0.40 |

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | |
|---|---|
| | Formulation B6 with Tinosorb S Lite Aqua |
| pH | 6.07 |
| consistency | viscous |
| Viskosität DVIII + RV6/10 rpm | 7160 mPa s |
| Calculated in silico SPF | 50 |
| In vitro SPF | 71 |

The sun protection formulation B6 according to the present invention shows higher SPF than calculated and expected.

| | Formulation B7: Spray, SPF 30 | | | |
|---|---|---|---|---|
| | | | Amount % w/w (as supplied) | |
| | Tradename | INCI-Name | B7-1 | B7-2 |
| A | Eumulgin ® SG | Sodium Stearoyl Glutamate | 2.00 | 2.00 |
| | Cetiol ® AB | C12-15 Alkyl Benzoate | 2.00 | 2.00 |
| | Cetiol ® B | Dibutyl Adipate | 2.00 | 2.00 |
| | Cetiol ® SN | Cetearyl Isononanoate | 2.00 | 2.00 |
| | Dermosoft ® Octiol | Caprylyl Glycol | 0.40 | 0.40 |
| | Uvinul ® N539T | OCR | 10.00 | 10.00 |
| | Neoheliopan ® OS | EHS | 5.00 | 5.00 |
| | Parsol ® 1789 | BMDBM | 5.00 | 5.00 |
| | Uvinul ® A Plus | Diethylamino Hydroxybenzoyl Hexyl Benzoate | 4.90 | 4.90 |
| | Tinosorb ® S | BEMT | 1.00 | 1.00 |
| B | Water | Aqua | 27.8 | 27.8 |

| Formulation B7: Spray, SPF 30 | | | | |
|---|---|---|---|---|
| | | | Amount % w/w (as supplied) | |
| | Tradename | INCI-Name | B7-1 | B7-2 |
| | Glycerin | Glycerin | 6.00 | 6.00 |
| | Edeta ® BD | Disodium EDTA | 0.20 | 0.20 |
| | Pemulen ® TR-2 | Acrylates/C10-30 Alkyl Acrylate Crosspolymer | 0.10 | 0.10 |
| | Rheocare ® TTA | Acrylates Copolymer | 0.50 | 0.50 |
| C | Eusolex ® 232 | Phenylbenzimidazole Sulfonic Acid | 0.50 | 0.50 |
| | Water | water | 5.00 | 5.00 |
| | Tris-amino ultra pure | Tromethamine | 0.40 | 0.40 |
| D | Tinosorb ® S Aqua | Aqua (and) Bis-Ethylhexyloxyphenol Methoxyphenyl Triazine (and) Polymethyl Methacrylate | 10.00 | |
| | Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 |
| | Cetiol ® Ultimate | Cyclohexasiloxane (and) Cyclopentasiloxane | 5.00 | 5.00 |
| E | Ethanol | Ethanol | 5.00 | 5.00 |
| | Water | Aqua | 5.00 | 5.00 |

Viscosity of the formulations was determined.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | Formulation B7-1 with Tinosorb S Aqua | Formulation B7-2 with Tinosorb S Lite Aqua |
|---|---|---|
| pH | 7.7 | 7.8 |
| Viscosity DVIII + LV/Sp2 + 3/10 rpm 1 d | 7282 | 1188 |
| Viscosity DVIII + LV/SP3/10 rpm 10 weeks | Lump formation, measurement difficult, <15000 | 9897 |
| Calculated in silico SPF (Sun Protection Factor) | 30 | 30 |
| reached SPF (Sun Protection Factor) for labeling | Lump formation, no measurement possible | 50 |

The formulation B7-2 according to the present invention shows better stability in combination with glycerine and ethanol compared to state of the art formulation B7-1, as well as unexpected high SPF compared to calculated values.

| Formulation B8: OMC free base, SPF 15 | | | | |
|---|---|---|---|---|
| | Tradename | INCI-Name | Formulation B8-1 with Tinosorb S Aqua amount % w/w (as supplied) | Formulation B8-2 with Tinosorb S Lite Aqua amount % w/w (as supplied) |
| A | Cetiol ® B | Dibutyl Adipate | 7.00 | 7.00 |
| | Euxyl ® PE 9010 | Phenoxyethanol (and) Ethylhexylglycerin | 1.00 | 1.00 |
| | Uvinul ® T150 | EHT | 2.00 | 2.00 |
| | Uvinul ® A Plus | DHHB | 3.00 | 3.00 |
| | Neo heliopan ® OS | EHS | 5.00 | 5.00 |
| | Tinosorb ® S | BEMT | 2.00 | |
| B | Water | Aqua | 75.20 | 67.40 |
| | Glycerin | Glycerin | 2.00 | 2.00 |
| | EDTA BD | Dissodium EDTA | 0.20 | 0.20 |
| C | Cosmedia ® ACE | Sodium Polyacrylate, Dicaprylyl Carbonate, Polyglyceryl-3 Caprate | 2.00 | 2.00 |
| D | Tinosorb ® S Aqua | Aqua (and) Bis-Ethylhexyloxyphenol Methoxyphenyl Triazine (and) Polymethyl Methacrylate | 10.00 | |

Formulation B8: OMC free base, SPF 15

| Tradename | INCI-Name | Formulation B8-1 with Tinosorb S Aqua amount % w/w (as supplied) | Formulation B8-2 with Tinosorb S Lite Aqua amount % w/w (as supplied) |
|---|---|---|---|
| Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 |
| NaOH 30% | | 0.60 | 0.40 |

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

Specification

| | Formulation B8-1 with Tinosorb S Aqua | Formulation B8-2 with Tinosorb S Lite Aqua |
|---|---|---|
| Calculated in silico SPF (Sun Protection Factor) | 20 | 24 |
| In vitro SPF | 10 | 25 |
| In vivo SPF (Dermscan) | 13.1, +/−2.4 | 22.7 +/− 2.2 |

The formulation B8-2 according to the present invention shows far better sun protection performance compared to state of the art formulation B8-1.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

The water resistance was determined according to internal method 50 (in vitro water resistance).

Specification

| | Formulation B9-1 with PBSA | Formulation B9-2 with Tinosorb S Lite Aqua | Formulation B9-3 with Tinosorb S Lite Aqua |
|---|---|---|---|
| In vitro SPF | 35.9 | 62.5 | 84 |
| SPF recovery | 7% | 31% | 86% |
| Water resistance | no | no | yes |

The formulations B9-2 and B9-3 according to the present invention show far better sun protection performance com- Formulation B9: sun screen formulation, SPF 50+

| | Tradename | INCI-Name | Formulation B9-1 with PBSA Amount % w/w (as supplied) | Formulation B9-2 Tinosorb S Lite Aqua Amount % w/w (as supplied) | Formulation B9-3 with Tinosorb S Lite Aqua Amount % w/w (as supplied) |
|---|---|---|---|---|---|
| A | Eumulgin ® VL 75 | | 2.00 | 2.00 | 2.00 |
| | Eumulgin ® SG | Sodium Stearoyl Glutamate | 0.50 | 0.50 | 0.50 |
| | Cetiol ® AB | C12-15 Alkyl Benzoate | 6.00 | 6.00 | 6.00 |
| | Cetiol ® CC | Dicaprylyl Carbonate | 6.00 | 6.00 | 6.00 |
| | Cetiol ® B | Dibutyl Adipate | 8.00 | 8.00 | 8.00 |
| | Cetiol ® OE | Dicaprylyl Ether | 4.00 | 4.00 | 4.00 |
| | Euxyl ® PE 9010 | Phenoxyethanol (and) Ethylhexylglycerin | 1.00 | 1.00 | 1.00 |
| | Uvinul ® T150 | EHT | 3.00 | 3.00 | 3.00 |
| | Tinosorb ® S | BEMT | 2.00 | 3.00 | 3.00 |
| | Uvinul ® A Plus | DHHB | 8.00 | 8.00 | 6.00 |
| | Uvasorb ® HEB | DBT | | | 3.00 |
| | Neoheliopan ® OS | EHS | | | 5.00 |
| B | Water | Aqua | 33.20 | 26.15 | 31.45 |
| | Glycerin | Glycerin | 2.00 | 2.00 | 2.00 |
| | Avicel ® PC 611 | Microcrystalline Cellulose | 1.00 | 1.00 | 1.00 |
| | EDTA BD | Disodium EDTA | 0.20 | 0.20 | 0.20 |
| | Mais PO4 PH "B" | Distarch Phosphate | 5.00 | 5.00 | 5.00 |
| C | Eusolex ® 232 | PBSA | 4.50 | 3.00 | |
| | L-Arginine | | 2.60 | 1.95 | |
| | Water | Aqua | 10.00 | 10.00 | |
| D | Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 | 12.50 |
| | Cetiol ® Ultimate | Undecane, Tridecane | 2.00 | 2.00 | 2.00 |
| | Acid citric 30% | | | 0.20 | 0.35 | pared to state of the art formulation B9-1. The water resistance is also better and can be further improved from 31% to 86% SPF recovery by increasing the amount of Tinosorb S Lite Aqua from 10% to 12.5%.

Formulation B10: Sun gel formulation

| | Tradename | INCI-Name | Formulation B10-1 with Tinosorb S Aqua Amount % w/w (as supplied) | Formulation B10-2 with Tinosorb S Lite Aqua Amount % w/w (as supplied) |
|---|---|---|---|---|
| A | Eumulgin® prisma | Disodium Cetearyl Sulfosuccinate | 1.00 | 1.00 |
| | Cetiol® B | Dibutyl Adipate | 5.00 | 5.00 |
| | Cetiol® AB | C12-15 Alkyl Benzoate | 5.00 | 5.00 |
| | Cetiol® CC | Dicaprylyl Carbonate | 5.00 | 5.00 |
| | Cetiol® Ultimate | Undecane, Tridecane | 2.00 | 2.00 |
| | Euxyl® PE9010 | Phenoxyethanol, Ethylhexylglycerin | 1.00 | 1.00 |
| B | Water | Aqua | 68.36 | 68.36 |
| | EDTA BD | Dissodium EDTA | 0.10 | 0.10 |
| | Rheocare® TTA | Acrylates Copolymer | 2.00 | 2.00 |
| C | NaOH 30% | | 0.54 | 0.54 |
| D | Tinosorb® S Aqua | Aqua (and) Bis-Ethylhexyloxyphenol Methoxyphenyl Triazine (and) Polymethyl Methacrylate | 10.00 | |
| | Tinosorb® S Lite Aqua | Aqua (and) Bis-Ethylhexyloxyphenol Methoxyphenyl Triazine (and) Acrylates/C12-22 Alkyl Methacrylate Copolymer | | 10.00 |

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | Formulation B10-1 with Tinosorb S Aqua | Formulation B10-2 with Tinosorb® S Lite Aqua |
|---|---|---|
| pH | 6.93 | 7.29 |
| Viscosity RV6 10 rpm, 1 day | 3600 | 1600 |
| Aspect, 1 day | fluid | fluid |
| Aspect after 1 months | Phase separation oil/water | Stable gel |
| Aspect after 3 months | Measurement not possible | Stable gel |

The formulation B10-2 according to the present invention shows better stability compared to state of the art formulation B10-1.

Formulation B11: Sun gel formulation

| | Tradename | INCI-Name | Formulation B11-1 with Tinosorb S Aqua Amount % w/w (as supplied) | Formulation B11-2 with Tinosorb S Lite Aqua Amount % w/w (as supplied) |
|---|---|---|---|---|
| A | Eumulgin® SG | Sodium Stearoyl Glutamate | 1.00 | 1.00 |
| | Cetiol® B | Dibutyl Adipate | 5.00 | 5.00 |
| | Cetiol® AB | C12-15 Alkyl Benzoate | 5.00 | 5.00 |
| | Cetiol® CC | Dicaprylyl Carbonate | 5.00 | 5.00 |
| | Cetiol® Ultimate | Undecane, Tridecane | 2.00 | 2.00 |
| | Euxyl® PE9010 | Phenoxyethanol, Ethylhexylglycerin | 1.00 | 1.00 |
| B | Water | Aqua | 68.36 | 68.36 |
| | EDTA BD | Dissodium EDTA | 0.10 | 0.10 |
| | Rheocare® TTA | Acrylates Copolymer | 2.00 | 2.00 |

| Formulation B11: Sun gel formulation | | | |
|---|---|---|---|
| Tradename | INCI-Name | Formulation B11-1 with Tinosorb S Aqua Amount % w/w (as supplied) | Formulation B11-2 with Tinosorb S Lite Aqua Amount % w/w (as supplied) |
| C NaOH 30% | | 0.54 | 0.54 |
| D Tinosorb ® S Aqua | Aqua (and) Bis-Ethylhexyloxyphenol Methoxyphenyl Triazine (and) Polymethyl Methacrylate | 10.00 | |
| Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 |

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | | |
|---|---|---|
| | Formulation B11-1 with Tinosorb ® S Aqua | Formulation B11-2 with Tinosorb ® S Lite Aqua |
| pH | 6.83 | 7.10 |
| Viscosity RV6 10 rpm, 1 day | 1340 | 1200 |
| Aspect, 1 day | fluid | fluid |
| Aspect after 1 months | Phase separation | Stable gel |

The formulation B11-2 shows better stability compared to state of the art formulation B11-1.

The samples are applied on sand blasted PMMA plates (delivered by Helioscience, Marseille, France) with a concentration of 1.4 mg/cm$^2$, irradiated with an Atlas CPS+ Irradiator and tested in an Optometrics SPF 290 analyzer. The testing procedure is carried out according to DIN 67502. The calculation of the in vitro SPF is done according to M. Wloka et al., Proceedings of the 8$^{th}$ International Conference, The Royal Society, London, Paper 12.

| Specification | | |
|---|---|---|
| | Formulation B12-1 with Tinosorb S Aqua | Formulation B12-2 with Tinosorb ® S Lite Aqua |
| pH | Measurement not possible | 6.95 |
| Viscosity RV6 10 rpm, 1 day | Measurement not possible | 40960 |
| Aspect, 1 day | Solid, broken gel | gel |
| Aspect after 3 months | Measurement not possible | Stable gel |

The formulation B12-2 according to the present invention shows better stability compared to state of the art formulation B12-1.

| Formulation B12: Sun gel formulation | | | |
|---|---|---|---|
| Tradename | INCI-Name | Formulation B12-1 with Tinosorb ® S Aqua Amount % w/w (as supplied) | Formulation B12-2 with Tinosorb ® S Lite Aqua Amount % w/w (as supplied) |
| A Eumulgin ® SG | Sodium Stearoyl Glutamate | 1.00 | 1.00 |
| Cetiol ® B | Dibutyl Adipate | 5.00 | 5.00 |
| Cetiol ® AB | C12-15 Alkyl Benzoate | 5.00 | 5.00 |
| Cetiol ® CC | Dicaprylyl Carbonate | 5.00 | 5.00 |
| Cetiol ® Ultimate | Undecane, Tridecane | 2.00 | 2.00 |
| Euxyl ® PE9010 | Phenoxyethanol, Ethylhexylglycerin | 1.00 | 1.00 |
| B Water | Aqua | 68.36 | 68.36 |
| EDTA BD | Dissodium EDTA | 0.10 | 0.10 |
| Rheocare ® TTA | Acrylates Copolymer | 2.00 | 2.00 |
| C NaOH 30% | | 0.54 | 0.54 |
| D Tinosorb ® S Aqua | Aqua (and) Bis-Ethylhexyloxyphenol Methoxyphenyl Triazine (and) Polymethyl Methacrylate | 10.00 | |
| Tinosorb ® S Lite Aqua | Aqua (and) Bis-Ethylhexyloxyphenol Methoxyphenyl Triazine (and) Acrylates/C12-22 Alkyl Methacrylate Copolymer | | 10.00 |

Tinosorb S Aqua used as state of the art UV absorber in Examples B1-B12 has the following composition:

| % | Ingredient |
|---|---|
| 20 | Bisethylhexyloxyphenol Methoxyphenyl Triazine (BEMT) |
| 19 | PMMA* |
| 61 | Water |
| 1.5 | Lauryl ether sulphate, sodium salt |
| <0.002 | Amino methyl propanol |
| <0.0015 | MIT/CIT (5-Chloro-2-Methyl-4-Isothiazolin-3-on and 2-Methyl-4-Isothiazolin-3-on (3:1)) |

| % | Monomer | Monomer Residual |
|---|---|---|
| 90.00 | MMA (Methyl methacrylate) | <1000 ppm |
| 8.00 | SMA (Stearyl methacrylate) | <1000 ppm |
| 2.00 | MAA (Methacrylic acid) | <1000 ppm |
| 0.30 | Butandiol diacrylate | <100 ppm |

*PMMA, Monomer composition:

Test for Anti-Pollen Efficacy in Sunscreen Products (In-Vitro)

The following formulations have been used:

Formulation UV-CN-17-AC010901 (According to the Invention)

| Pha. | Ingredients | INCI-Name/Chemical-Name | Wt % | Function |
|---|---|---|---|---|
| A | Cetiol ® B | Dibutyl Adipate | 6.00 | Emollients |
|  | Cetiol ® AB | C12-15 Alkyl Benzoate | 3.00 | Emollients |
|  | Uvinul ® MC 80 | Ethylhexyl Methoxycinnamate | 7.00 | UVB Filter |
|  | Uvinul ® N 539 T | Octocrylene | 3.00 | UVB Filter |
|  | Uvinul ® A Plus | Diethylamino Hydroxybenzoyl Hexyl Benzoate | 7.00 | UVA Filter |
|  | Eumulgin ® SG | Sodium Stearoyl Glutamate | 1.20 | Emulsifier (O/W) |
| B | Water | Water | Qsp to 100 | Solvents |
|  | Butylene Glycol | Butylene Glycol | 4.00 | Active, humectant |
|  | Tinovis ® GTC UP | Acrylates/Beheneth-25 Methacrylate Copolymer | 2.00 | Rheology Modifier |
|  | Edeta ® BD | Disodium EDTA | 0.10 | Chelating Agents |
|  | Xanthan Gum | Xanthan Gum | 0.15 | Rheology Modifier |
| C | Sodium Hydroxide (10% solution) | Water (and) Sodium Hydroxide | 0.85 | Agent, pH adusting |
| D | Ethanol | Alcohol | 10.00 | Solvent |
| E | Cetiol ® Ultimate | Undecane (and) Tridecane | 4.00 | Emollients |
|  | DowCorning 9041 Silicone Elastomer Blend | Dimethicone (and) Dimethicone Crosspolymer | 2.00 | Skin feel modifier |
| F | Tinosorb ® S Lite Aqua | Aqua (and) Bis-Ethylhexyloxyphenol Methoxyphenyl Triazine (and) Acrylates/C12-22 Alkyl Methacrylate Copolymer | 5.00 | Broad Spectrum UV Filter |
|  | Orgasol ® 4000 EXD NAT | Nylon-6/12 | 2.00 | Opacifying Agents |

Formulation UV-CN-16-AC112901 (Comparison)

| Pha. | Ingredients | INCI-Name/Chemical-Name | Wt % | Function |
|---|---|---|---|---|
| A | Cetiol ® B | Dibutyl Adipate | 6.00 | Emollients |
|  | Cetiol ® AB | C12-15 Alkyl Benzoate | 3.00 | Emollients |
|  | Uvinul ® MC 80 | Ethylhexyl Methoxycinnamate | 7.00 | UVB Filter |
|  | Tinosorb ® S | Bis-Ethylhexyloxyphenol Methoxyphenyl Triazine | 1.50 | Broad Spectrum UV Filter |
|  | Uvinul ® N 539 T | Octocrylene | 3.00 | UVB Filter |
|  | Uvinul ® A Plus | Diethylamino Hydroxybenzoyl Hexyl Benzoate | 7.00 | UVA Filter |
| B | Water | Water | Qsp to 100 | Solvents |
|  | Butylene Glycol | Butylene Glycol | 4.00 | Active, humectant |
|  | Tinovis ® GTC UP | Acrylates/Beheneth-25 Methacrylate Copolymer | 2.00 | Rheology Modifier |
|  | Edeta ® BD | Disodium EDTA | 0.10 | Chelating Agents |
|  | Xanthan Gum | Xanthan Gum | 0.15 | Rheology Modifier |
| C | Eumulgin ® SG | Sodium Stearoyl Glutamate | 1.20 | Emulsifier (O/W) |
| D | Ethanol | Alcohol | 10.00 | Solvent |

| Pha. | Ingredients | INCI-Name/Chemical-Name | Wt % | Function |
|---|---|---|---|---|
| E | Cetiol ® Ultimate | Undecane (and) Tridecane | 4.00 | Emollients |
|  | DowCorning 9041 Silicone Elastomer Blend | Dimethicone (and) Dimethicone Crosspolymer | 2.00 | Skin feel modifier |
| F | Orgasol ® 4000 EXD NAT | Nylon-6/12 | 2.00 | Opacifying Agents |

The difference in both formulas is that Formulation UV-CN-16-AC112901 (comparison) does not contain the Tinosorb S Lite Aqua polymeric dispersion of the present invention.

The anti-pollen efficacy of the compositions has been tested on a PMMA board uniformly coated with 6 g of either UV-CN-17-AC010901 (according to the invention) or Formulation UV-CN-16-AC112901 (comparison). The board was put in an oven at 38° C. for 30 minutes.

As a pollen, fir pollen, diameter appr. 5 μm has been used. 0.2 g of pollen in a petri dish was evenly contacted with the PMMA boards. The petri dishes were weighted and the remaining pollen on the PMMA boards was measured. The following calculation has been used for the pollen attachment on the boards:

Remaining pollen on the PMMA board/applied pollen (in %)

A lower value indicates that less pollen stays on the boards.

The test result is shown in FIG. 1. Clearly, as can be taken from the different height of the bars, formulation UV-CN-17-AC010901 (according to the invention) shows a 35% improved anti-pollen efficacy than UV-CN-16-AC112901 (comparison).

Test for Anti-Oxidation Effect on Sebum (In-Vitro)

The following formulations have been used:

Formulation UV-CN-17-AC010901 (According to the Invention)

| Pha. | Ingredients | INCI-Name/Chemical-Name | Wt % | Function |
|---|---|---|---|---|
| A | Cetio ® B | Dibutyl Adipate | 6.00 | Emollients |
|  | Cetiol ® AB | C12-15 Alkyl Benzoate | 3.00 | Emollients |
|  | Uvinul ® MC 80 | Ethylhexyl Methoxycinnamate | 7.00 | UVB Filter |
|  | Uvinul ® N 539 T | Octocrylene | 3.00 | UVB Filter |
|  | Uvinul ® A Plus | Diethylamino Hydroxybenzoyl Hexyl Benzoate | 7.00 | UVA Filter |
|  | Eumulgin ® SG | Sodium Stearoyl Glutamate | 1.20 | Emulsifier (O/W) |
| B | Water | Water | Qsp to 100 | Solvents |
|  | Butylene Glycol | Butylene Glycol | 4.00 | Active, humectant |
|  | Tinovis ® GTC UP | Acrylates/Beheneth-25 Methacrylate Copolymer | 2.00 | Rheology Modifier |
|  | Edeta ® BD | Disodium EDTA | 0.10 | Chelating Agents |
|  | Xanthan Gum | Xanthan Gum | 0.15 | Rheology Modifier |
| C | Sodium Hydroxide (10% solution) | Water (and) sodium Hydroxide | 0.85 | Agent, pH adusting |
| D | Ethanol | Alcohol | 10.00 | Solvent |
| E | Cetiol ® Ultimate | Undecane (and) Tridecane | 4.00 | Emollients |
|  | DowCorning 9041 Silicone Elastomer Blend | Dimethicone (and) Dimethicone Crosspolymer | 2.00 | Skin feel modifier |
| F | Tinosorb ® S Lite Aqua | Aqua (and) Bis-Ethylhexyloxyphenol Methoxyphenyl Triazine (and) Acrylates/C12-22 Alkyl Methacrylate Copolymer | 5.00 | Broad Spectrum UV Filter |
|  | Orgasol 4000 EXD NAT | Nylon-6/12 | 2.00 | Opacifying Agents |

Formulation UV-CN-16-AC112901 (Comparison)

| Pha. | Ingredients | INCI-Name/Chemical-Name | Wt % | Function |
|---|---|---|---|---|
| A | Cetiol ® B | Dibutyl Adipate | 6.00 | Emollients |
|  | Cetiol ® AB | C12-15 Alkyl Benzoate | 3.00 | Emollients |
|  | Uvinul ® MC 80 | Ethylhexyl Methoxycinnamate | 7.00 | UVB Filter |

-continued

| Pha. | Ingredients | INCI-Name/Chemical-Name | Wt % | Function |
|---|---|---|---|---|
| | Tinosorb ® S | Bis-Ethylhexyloxyphenol Methoxyphenyl Triazine | 1.50 | Broad Spectrum UV Filter |
| | Uvinul ® N 539 T | Octocrylene | 3.00 | UVB Filter |
| | Uvinul ® A Plus | Diethylamino Hydroxybenzoyl Hexyl Benzoate | 7.00 | UVA Filter |
| B | Water | Water | Qsp to 100 | Solvents |
| | Butylene Glycol | Butylene Glycol | 4.00 | Active, humectant |
| | Tinovis ® GTC UP | Acrylates/Beheneth-25 Methacrylate Copolymer | 2.00 | Rheology Modifier |
| | Edeta ® BD | Disodium EDTA | 0.10 | Chelating Agents |
| | Xanthan Gum | Xanthan Gum | 0.15 | Rheology Modifier |
| C | Eumulgin ® SG | Sodium Stearoyl Glutamate | 1.20 | Emulsifier (O/W) |
| D | Ethanol | Alcohol | 10.00 | Solvent |
| E | Cetiol ® Ultimate | Undecane (and) Tridecane | 4.00 | Emollients |
| | DowCorning 9041 Silicone Elastomer Blend | Dimethicone (and) Dimethicone Crosspolymer | 2.00 | Skin feel modifier |
| F | Orgasol ® 4000 EXD NAT | Nylon-6/12 | 2.00 | Opacifying Agents |

The difference in both formulas is that Formulation UV-CN-16-AC112901 (comparison) does not contain the Tinosorb® S Lite Aqua polymeric dispersion of the present invention.

A sebum film has been prepared in a petri dish by using a solution of 1 g sebum in 100 ml ethanol. Ethanol was evaporated under nitrogen remaining 10 mg sebum film in the petri dish. 60 g of either UV-CN-17-AC010901 (according to the invention) or Formulation UV-CN-16-AC112901 (comparison) were applied on the sebum film petri dish and uniformly distributed. The short outer side of the petri dish was covered with an aluminium foil. The dish was put in a chamber to irridate the dish with an UV lamp in CPC for 2 hours.

After irridation the sebum was collected from the petri dish by adding 10 ml heptane. The amount of malondialdehyde (MDA) was measured by using the TBARS method. MDA is the oxidation product of sebum. The absorbance measurement was done at A=532 nm.

In FIG. 2 the anti-oxidation efficacy of the following three test formulations has been tested:
Formulation UV-CN-17-AC010901 (according to the invention)
Formulation UV-CN-16-AC112901 (comparison)—no Tinosorb S Lite Aqua polymeric dispersion
Base: Control without any sunscreen formulation As can be easily seen the Formulation UV-CN-17-AC010901 with Tinosorb S Lite Aqua shows a better anti-oxidation efficacy than Formulation UV-CN-16-AC112901 (appr. 25% better). The control has the highest MDA amount with the worst anti-oxidation efficacy.

Test for Reduction of Sand Adhesiveness on the Skin (In Vitro)

Formulations 112901 A and C (according to the invention)
Formulation 112901 (comparison)

| Ingredients | INCI-Name/Chemical-Name | 112901 | 112901A | 112901C | Function |
|---|---|---|---|---|---|
| Cetiol ® B | Dibutyl Adipate | 6.00 | 6.00 | 2.00 | Emollients |
| Cetiol ® AB | C12-15 Alkyl Benzoate | 3.00 | 3.00 | — | Emollients |
| Cetiol ® ININ | Isononyl Isononanoate | — | — | 4.00 | Emollients |
| Uvinul ® MC 80 | Ethylhexyl Methoxycinnamate | 7.00 | 7.00 | 10.00 | UVB Filter |
| Uvinul ® A Plus | Diethylamino Hydroxybenzoyl Hexyl Benzoate | 7.00 | 7.00 | 7.00 | UVA Filter |
| Tinosorb ® S | Bis-Ethylhexyloxyphenol Methoxyphenyl Triazine | 1.50 | — | — | BroadSpectrum UV Filter |
| Uvinul ® N 539 T | Octocrylene | 3.00 | 3.00 | — | UVB Filter |
| Eumulgin ® SG | Sodium Stearoyl Glutamate | 1.20 | 1.20 | 1.20 | Emulsifier (O/W) |
| Water | Water | Qsp to 100 | Qsp to 100 | Qsp to 100 | Solvents |
| Butylene Glycol | Butylene Glycol | 4.00 | 4.00 | 4.00 | Active, humectant |
| Tinovis ® GTC UP | Acrylates/Beheneth-25 Methacrylate Copolymer | 2.00 | 2.00 | 2.00 | Rheology Modifier |
| Edeta ® BD | Disodium EDTA | 0.10 | 0.10 | 0.10 | Chelating Agents |
| Pluracare ® E 1500 | PEG-32 | — | — | 2.00 | Active, humectant |
| Xanthan Gum | Xanthan Gum | 0.15 | 0.15 | 0.15 | Rheology Modifier |

| Ingredients | INCI-Name/Chemical-Name | 112901 | 112901A | 112901C | Function |
|---|---|---|---|---|---|
| Sodium Hydroxide (10% solution) | Water (and) sodium Hydroxide | | 0.85 | 0.85 | Agent, pH adusting |
| Ethanol | Alcohol | 10.00 | 10.00 | 10.00 | Solvent |
| Orgasol® 4000 EXD | Nylon 6/12 | 2.00 | 2.00 | 2.00 | Opacifying Agents |
| Purisoft® POE LS 9726 | Water (and) Glycerin (and) *Moringa Oleifera* Seed Extract | — | — | 3.00 | Active, skin conditioning |
| Cetiol® Ultimate | Undecane (and) Tridecane | 4.00 | 4.00 | 4.00 | Emollients |
| DowCorning 9041 Silicone Elastomer Blend | Dimethicone (and) Dimethicone Crosspolymer | 2.00 | 2.00 | 2.00 | Skin feel modifier |
| Tinosorb® S Lite Aqua | Aqua (and) Bis-Ethylhexyloxyphenol Methoxyphenyl Triazine (and) Acrylates/C12-22 Alkyl Methacrylate Copolymer | — | 5.00 | 5.00 | BroadSpectrum UV Filter |

The difference in the formulas is that Formulation 112901 (comparison) does not contain the Tinosorb S Lite Aqua polymeric dispersion of the present invention.

The suncare compositions have been tested on a PMMA board by uniformly applying 6 g of the product thereon. The coated board was put in an oven at 38° C. for 30 minutes. Then the board was contacted for 30 s with sand being kept in a petri dish in a turnover procedure. The sand remained in the dish was weighed again. The following calculation has been used for the sand attachment on the boards:

Remaining sand on the PMMA board/applied sand (in %)

A lower value indicates that less sand stays on the boards.

In FIG. 3, the adhesion ratio between the sunscreen compositions 112901 A and 112901 is shown. Clearly, sunscreen composition 112901 A containing the Tinosorb S Lite Aqua aqueous solution exhibits a 30% sand adhesiveness reduction with identical UV protection.

The invention claimed is:

1. An aqueous polymer dispersion with an average particle size of less than 1000 nm comprising
   a) a polymer carrier which is an acrylate/$C_{12}$-$C_{22}$ alkyl methacrylate copolymer;
   b) an oil-soluble organic UV absorber corresponding to the compound of formula

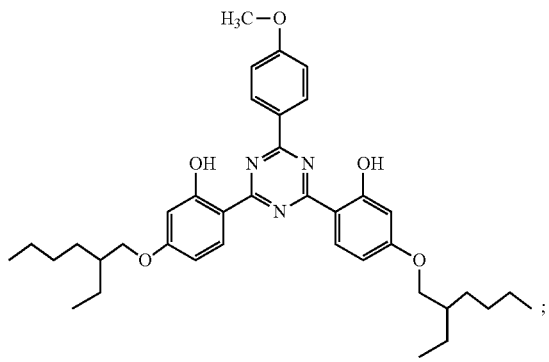 [SMILES: CCCCC(CC)COc1ccc(-c2nc(-c3ccc(OC)cc3)nc(-c3ccc(OCC(CC)CCCC)cc3O)n2)c(O)c1]

wherein the weight ratio of the oil-soluble organic UV absorber (b) to polymer carrier (a) is greater than 50 parts UV absorber per 100 parts of carrier; and
   c) a surfactant which comprises
   $c_1$) a nonionic surfactant selected from the group consisting of lauryl glucoside, coco-glucoside, sucrose polystearate and decyl glucoside
   and
   $c_2$) an anionic surfactant selected from the group consisting of lauryl sulfosuccinate, cetyl sulfosuccinate, stearyl sulfosuccinate, and mixtures thereof.

2. The dispersion according to claim 1, wherein the average particle size of the aqueous polymer dispersion is less than 500 nm.

3. The dispersion according to claim 1, wherein the concentration of the polymer carrier with oil-soluble organic UV absorber (b) in the dispersion is from 20% to 60% b.w.

4. The dispersion according to claim 1, wherein the surfactant further comprises sodium cetearyl sulfate.

5. A cosmetic composition comprising
   (A) a concentrated aqueous polymer dispersion according to claim 1;
   (B) a cosmetically acceptable carrier; and optionally
   (C) ethanol.

* * * * *